US012582505B2

(12) United States Patent
Matov et al.

(10) Patent No.: US 12,582,505 B2
(45) Date of Patent: *Mar. 24, 2026

(54) ORTHODONTIC ALIGNERS AND METHODS OF DESIGNING AND FABRICATING ORTHODONTIC ALIGNERS BASED ON TOOTH SHAPE

(71) Applicant: ALIGN TECHNOLOGY, INC., San Jose, CA (US)

(72) Inventors: Vadim Matov, San Jose, CA (US); John Y. Morton, San Jose, CA (US); Eric Kuo, San Jose, CA (US); Heng Cao, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 19/015,314

(22) Filed: Jan. 9, 2025

(65) Prior Publication Data

US 2025/0143842 A1 May 8, 2025

Related U.S. Application Data

(60) Continuation of application No. 17/990,160, filed on Nov. 18, 2022, which is a continuation of application (Continued)

(51) Int. Cl.
*A61C 7/08* (2006.01)
*A61B 6/03* (2006.01)

(Continued)

(52) U.S. Cl.
CPC .............. *A61C 7/002* (2013.01); *A61B 6/032* (2013.01); *A61B 6/51* (2024.01); *A61C 7/00* (2013.01);

(Continued)

(58) Field of Classification Search
CPC .................................. A61C 7/002; A61C 7/08
See application file for complete search history.

(56) References Cited

U.S. PATENT DOCUMENTS 6,702,575 B2 * 3/2004 Hilliard .................... A61C 7/08
433/18
6,830,450 B2 * 12/2004 Knopp .................... B29C 43/56
433/18

(Continued)

*Primary Examiner* — Ralph A Lewis
(74) *Attorney, Agent, or Firm* — FisherBroyles, LLP

(57) ABSTRACT

A series of orthodontic aligners may be produced by a process including receiving a first position of at least one tooth of a patient for a first treatment stage of plurality of orthodontic treatment stages, determining a movement vector magnitude and direction for moving the at least one tooth from the first position towards a second position, analyzing a surface of the at least one tooth of the patient based on the determined movement vector, designing a first orthodontic aligner of the series of orthodontic aligners based on the analysis of the surface of the at least one tooth of the patient so that a physical orthodontic aligner, when in position on teeth of the patient at the first treatment stage, moves the at least one tooth from the first position towards the second position along the determined movement vector, and fabricating the physical orthodontic aligner.

20 Claims, 28 Drawing Sheets

Related U.S. Application Data

No. 16/433,865, filed on Jun. 6, 2019, now Pat. No. 11,529,215, which is a continuation of application No. 14/796,773, filed on Jul. 10, 2015, now Pat. No. 11,571,277, which is a continuation of application No. 13/865,091, filed on Apr. 17, 2013, now Pat. No. 9,107,722, which is a division of application No. 12/346,735, filed on Dec. 30, 2008, now Pat. No. 8,439,672.

(60) Provisional application No. 61/024,526, filed on Jan. 29, 2008, provisional application No. 61/024,534, filed on Jan. 29, 2008.

(51) Int. Cl.

| | |
|---|---|
| *A61B 6/51* | (2024.01) |
| *A61C 7/00* | (2006.01) |
| *A61C 7/02* | (2006.01) |
| *A61C 7/14* | (2006.01) |
| *A61C 7/16* | (2006.01) |
| *A61C 7/20* | (2006.01) |
| *B33Y 80/00* | (2015.01) |

(52) U.S. Cl.
CPC .................. *A61C 7/02* (2013.01); *A61C 7/08* (2013.01); *A61C 7/146* (2013.01); *A61C 7/16* (2013.01); *A61C 7/20* (2013.01); *B33Y 80/00* (2014.12)

(56) References Cited

U.S. PATENT DOCUMENTS

| | | | | |
|---|---|---|---|---|
| 8,439,672 | B2 * | 5/2013 | Matov | A61C 7/00 433/24 |
| 9,107,722 | B2 * | 8/2015 | Matov | A61C 7/00 |
| 11,529,215 | B2 * | 12/2022 | Matov | A61C 7/146 |
| 11,571,277 | B2 * | 2/2023 | Matov | A61C 7/02 |
| 11,723,748 | B2 | 8/2023 | Li et al. | |
| 11,864,970 | B2 | 1/2024 | Shojaei et al. | |
| 11,903,793 | B2 | 2/2024 | Cramer et al. | |
| 12,048,605 | B2 | 7/2024 | Farkash et al. | |
| 12,076,207 | B2 | 9/2024 | Liu et al. | |
| 12,125,581 | B2 | 10/2024 | Slynko et al. | |
| 12,220,288 | B2 | 2/2025 | Chekh et al. | |
| 2004/0110110 | A1 * | 6/2004 | Chishti | B33Y 80/00 433/24 |
| 2006/0223022 | A1 * | 10/2006 | Solomon | A61C 7/08 433/8 |
| 2007/0065768 | A1 * | 3/2007 | Nadav | A61C 7/08 433/18 |
| 2022/0023002 | A1 | 1/2022 | Cramer et al. | |
| 2022/0079714 | A1 | 3/2022 | Paraketsov et al. | |
| 2022/0104920 | A1 | 4/2022 | Wang et al. | |
| 2022/0165388 | A1 | 5/2022 | Chernov et al. | |
| 2022/0262007 | A1 | 8/2022 | Cramer et al. | |
| 2022/0378549 | A1 | 12/2022 | Blanco et al. | |
| 2023/0008836 | A1 | 1/2023 | Yazykov et al. | |
| 2023/0056427 | A1 | 2/2023 | Blanco et al. | |
| 2023/0190411 | A1 | 6/2023 | Chiu et al. | |
| 2023/0225831 | A1 | 7/2023 | Cramer et al. | |
| 2023/0263594 | A1 | 8/2023 | Lobsiger et al. | |
| 2023/0301752 | A1 | 9/2023 | Wang et al. | |
| 2023/0325558 | A1 | 10/2023 | Kukk et al. | |
| 2023/0352150 | A1 | 11/2023 | Meyer et al. | |
| 2023/0414323 | A1 | 12/2023 | Sun et al. | |
| 2024/0033041 | A1 | 2/2024 | Chernov et al. | |
| 2024/0033045 | A1 | 2/2024 | Tanugula et al. | |
| 2024/0065807 | A1 | 2/2024 | Chang et al. | |
| 2024/0087184 | A1 | 3/2024 | Gao et al. | |
| 2024/0108436 | A1 | 4/2024 | Grebenkin et al. | |
| 2024/0122463 | A1 | 4/2024 | Li et al. | |
| 2024/0122677 | A1 | 4/2024 | Popov et al. | |
| 2024/0131795 | A1 | 4/2024 | Li et al. | |
| 2024/0144480 | A1 | 5/2024 | Seeber et al. | |
| 2024/0177397 | A1 | 5/2024 | Li et al. | |
| 2024/0185420 | A1 | 6/2024 | Cramer et al. | |
| 2024/0185518 | A1 | 6/2024 | Seeber et al. | |
| 2024/0189078 | A1 | 6/2024 | Cramer et al. | |
| 2024/0197449 | A1 | 6/2024 | Stroganov et al. | |
| 2024/0216106 | A1 | 7/2024 | Choi et al. | |
| 2024/0257342 | A1 | 8/2024 | Semenov et al. | |
| 2024/0277450 | A1 | 8/2024 | Sherstennikov et al. | |
| 2024/0293200 | A1 | 9/2024 | Kirsanov et al. | |

* cited by examiner

Slope = Performance Index $R^2$ = Predictability

| Type of Movement |
| --- |
| Expansion/Constriction (+/-X Translation) |
| Mesialization/Distalization (+/-Y Translation) |
| Intrusion (-Z Translation) |
| Extrusion (+Z Translation) |
| Tip/Angulation (X Rotation) |
| Torque/Inclination (Y Rotation) |
| Pure Rotation (Z Rotation) |

$$y = 0.8476x + 0.0277$$
$$R^2 = 0.8203$$

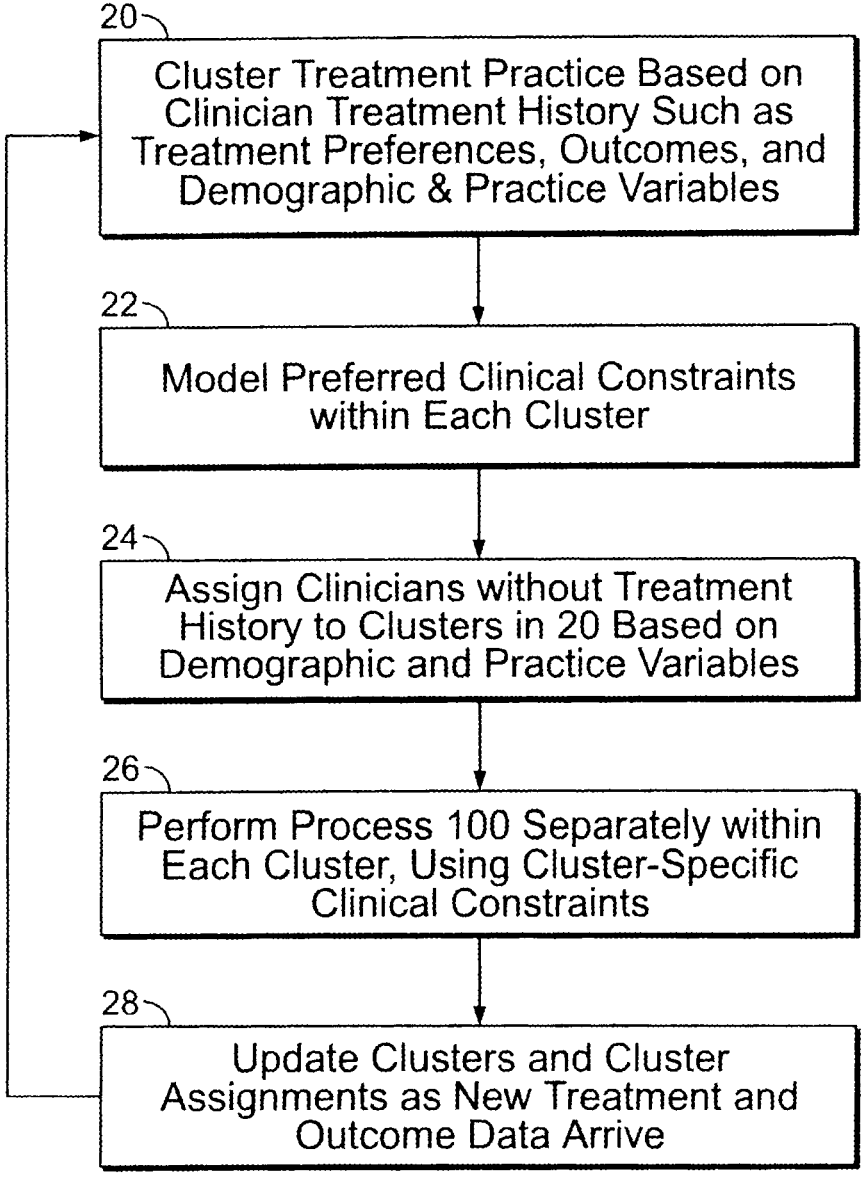

20 ⌐
Cluster Treatment Practice Based on
Clinician Treatment History Such as
Treatment Preferences, Outcomes, and
Demographic & Practice Variables 22 ⌐
Model Preferred Clinical Constraints
within Each Cluster 24 ⌐
Assign Clinicians without Treatment
History to Clusters in 20 Based on
Demographic and Practice Variables 26 ⌐
Perform Process 100 Separately within
Each Cluster, Using Cluster-Specific
Clinical Constraints 28 ⌐
Update Clusters and Cluster
Assignments as New Treatment and
Outcome Data Arrive

FIG. 1E

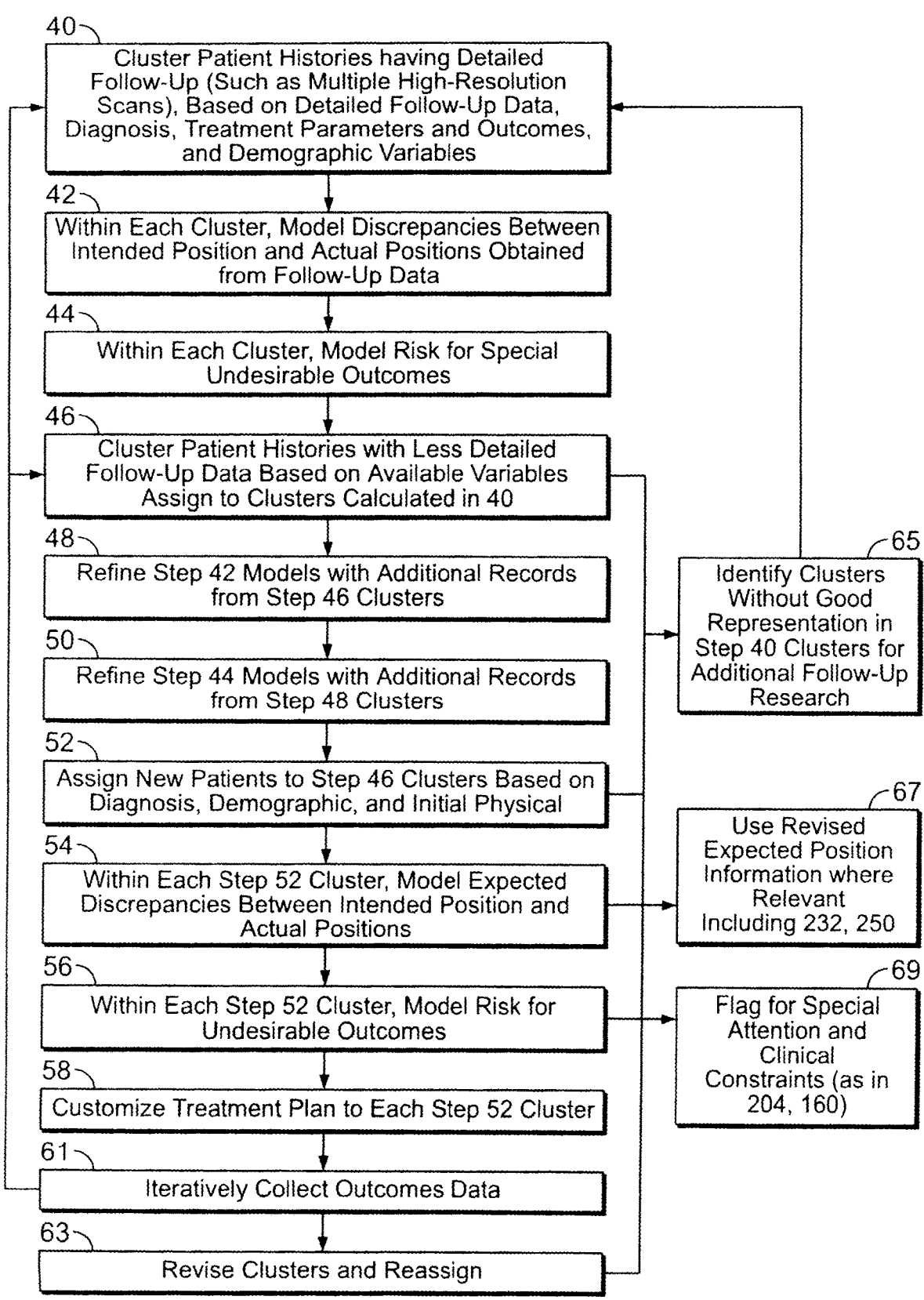

40 — Cluster Patient Histories having Detailed Follow-Up (Such as Multiple High-Resolution Scans), Based on Detailed Follow-Up Data, Diagnosis, Treatment Parameters and Outcomes, and Demographic Variables 42 — Within Each Cluster, Model Discrepancies Between Intended Position and Actual Positions Obtained from Follow-Up Data 44 — Within Each Cluster, Model Risk for Special Undesirable Outcomes 46 — Cluster Patient Histories with Less Detailed Follow-Up Data Based on Available Variables Assign to Clusters Calculated in 40

48 — Refine Step 42 Models with Additional Records from Step 46 Clusters

50 — Refine Step 44 Models with Additional Records from Step 48 Clusters

52 — Assign New Patients to Step 46 Clusters Based on Diagnosis, Demographic, and Initial Physical 54 — Within Each Step 52 Cluster, Model Expected Discrepancies Between Intended Position and Actual Positions 56 — Within Each Step 52 Cluster, Model Risk for Undesirable Outcomes 58 — Customize Treatment Plan to Each Step 52 Cluster 61 — Iteratively Collect Outcomes Data 63 — Revise Clusters and Reassign 65 — Identify Clusters Without Good Representation in Step 40 Clusters for Additional Follow-Up Research 67 — Use Revised Expected Position Information where Relevant Including 232, 250

69 — Flag for Special Attention and Clinical Constraints (as in 204, 160)

FIG. 1F

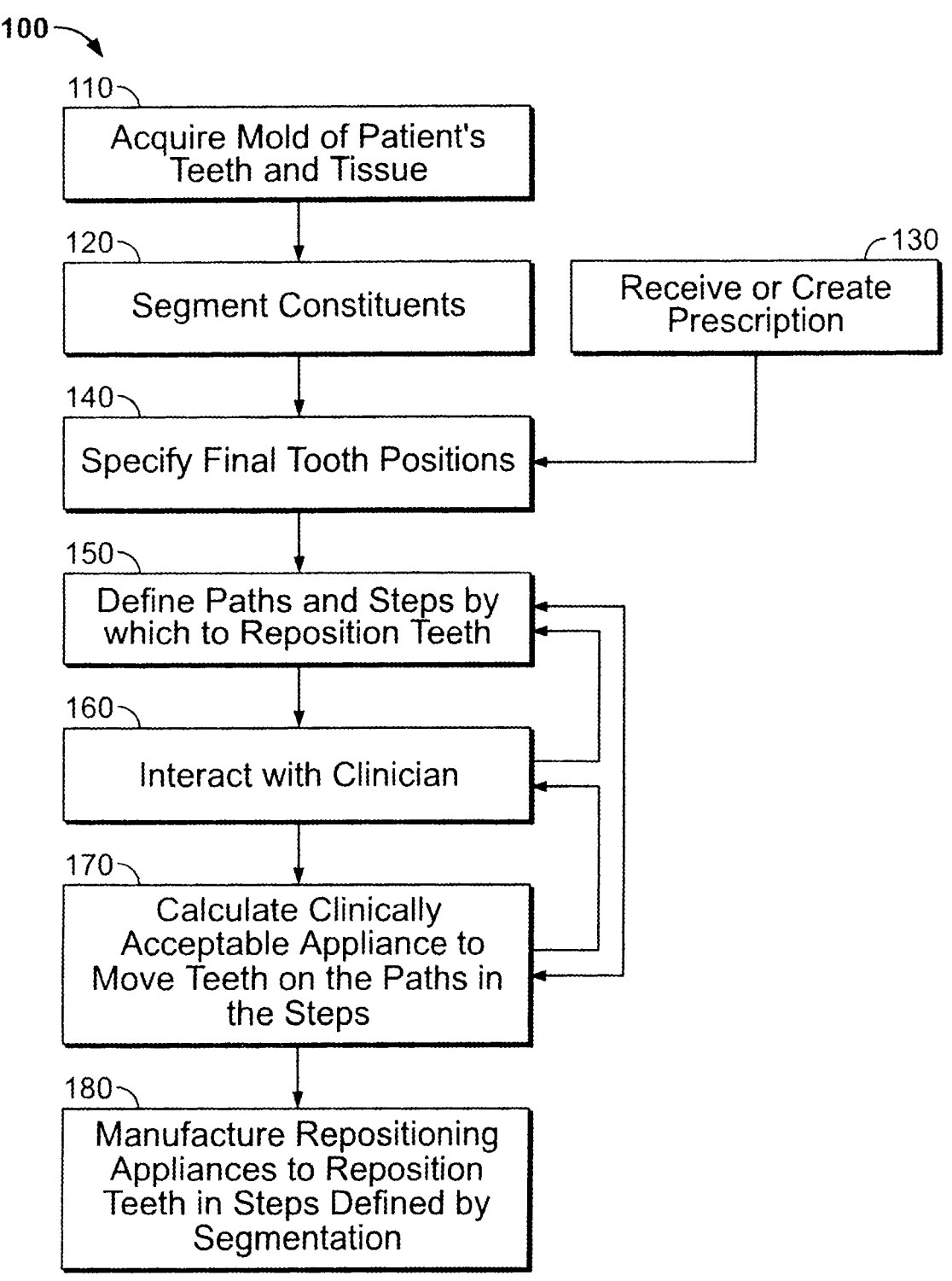

100

110 — Acquire Mold of Patient's Teeth and Tissue

120 — Segment Constituents

130 — Receive or Create Prescription

140 — Specify Final Tooth Positions

150 — Define Paths and Steps by which to Reposition Teeth

160 — Interact with Clinician

170 — Calculate Clinically Acceptable Appliance to Move Teeth on the Paths in the Steps 180 — Manufacture Repositioning Appliances to Reposition Teeth in Steps Defined by Segmentation

310
Create Finite Element Model of Initial Jaw

302
Input Data:

Initial Positions of Teeth

Shapes of Teeth

Shape and Viscosity of Embedding Fluid

Boundary Conditions

320
Cache for Reuse in Later Iterations

330
Create Finite Element Model of Aligner

304
Input Data:

Aligner Material

Aligner Shape

340
Place Model Aligner on Model Jaw to Create Composite Model of In-Place Aligner

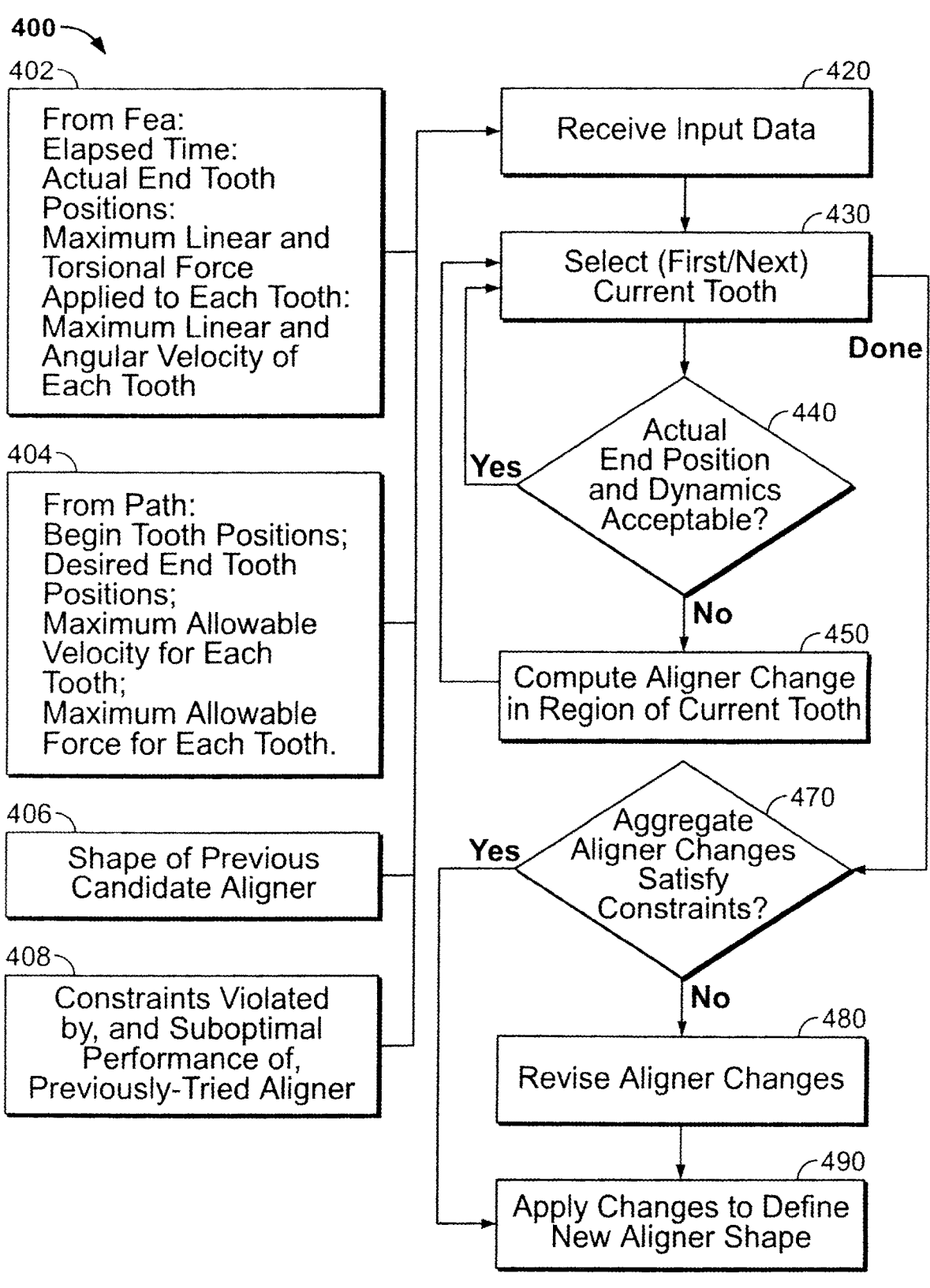

400

402
From Fea:
Elapsed Time:
Actual End Tooth
Positions:
Maximum Linear and
Torsional Force
Applied to Each Tooth:
Maximum Linear and
Angular Velocity of
Each Tooth 404
From Path:
Begin Tooth Positions;
Desired End Tooth
Positions;
Maximum Allowable
Velocity for Each
Tooth;
Maximum Allowable
Force for Each Tooth.

406
Shape of Previous
Candidate Aligner

408
Constraints Violated
by, and Suboptimal
Performance of,
Previously-Tried Aligner 420
Receive Input Data 430
Select (First/Next)
Current Tooth Done 440
Actual
End Position
and Dynamics
Acceptable?

Yes

No

450
Compute Aligner Change
in Region of Current Tooth

470
Aggregate
Aligner Changes
Satisfy
Constraints?

Yes

No

480
Revise Aligner Changes

490
Apply Changes to Define
New Aligner Shape

To Move Tooth
Along its Axis
Change Size of
Model Tooth
Defining Aligner

710 ⟍     712 ⟍     714 ⟍

−z direction

−x direction        +x direction

+z direction

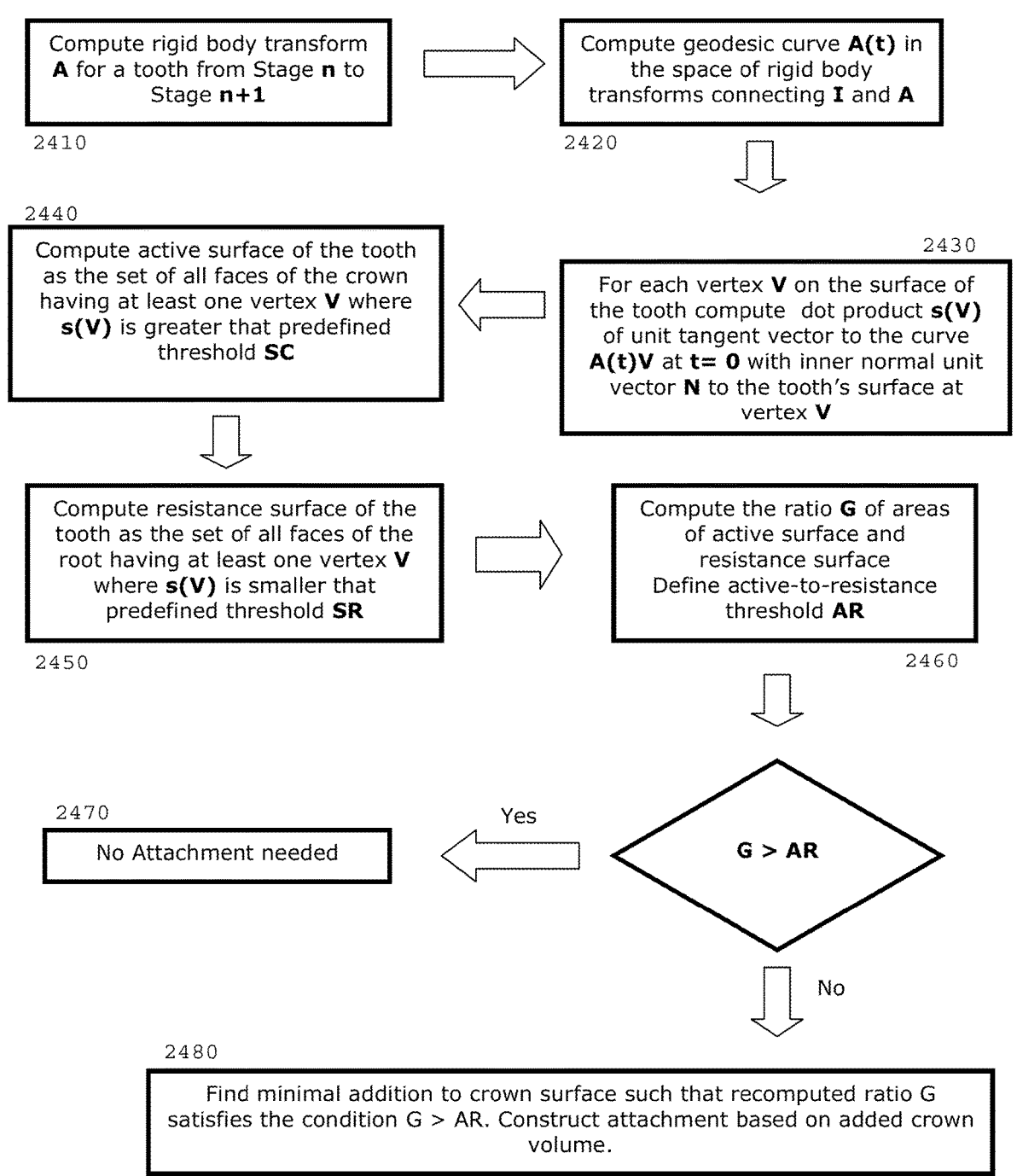

Compute rigid body transform A for a tooth from Stage n to Stage n+1

2410

Compute geodesic curve A(t) in the space of rigid body transforms connecting I and A

2420

2440

Compute active surface of the tooth as the set of all faces of the crown having at least one vertex V where s(V) is greater that predefined threshold SC

2430

For each vertex V on the surface of the tooth compute dot product s(V) of unit tangent vector to the curve A(t)V at t= 0 with inner normal unit vector N to the tooth's surface at vertex V

Compute resistance surface of the tooth as the set of all faces of the root having at least one vertex V where s(V) is smaller that predefined threshold SR

2450

Compute the ratio G of areas of active surface and resistance surface Define active-to-resistance threshold AR

2460

2470

No Attachment needed

Yes

G > AR

No

2480

Find minimal addition to crown surface such that recomputed ratio G satisfies the condition G > AR. Construct attachment based on added crown volume.

FIGURE 24

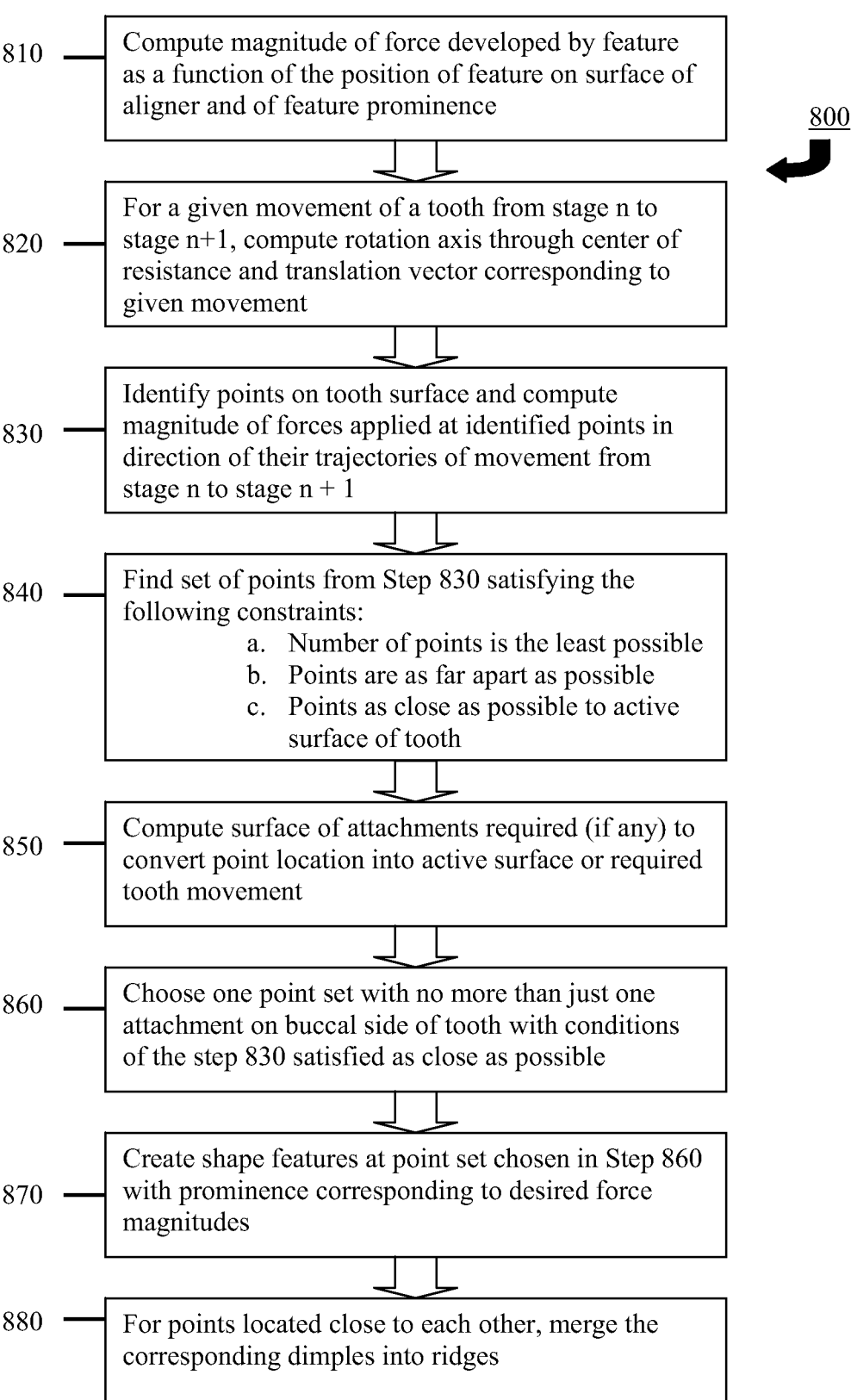

810 — Compute magnitude of force developed by feature as a function of the position of feature on surface of aligner and of feature prominence

800

820 — For a given movement of a tooth from stage n to stage n+1, compute rotation axis through center of resistance and translation vector corresponding to given movement 830 — Identify points on tooth surface and compute magnitude of forces applied at identified points in direction of their trajectories of movement from stage n to stage n + 1

840 — Find set of points from Step 830 satisfying the following constraints:
    a. Number of points is the least possible
    b. Points are as far apart as possible
    c. Points as close as possible to active surface of tooth 850 — Compute surface of attachments required (if any) to convert point location into active surface or required tooth movement 860 — Choose one point set with no more than just one attachment on buccal side of tooth with conditions of the step 830 satisfied as close as possible 870 — Create shape features at point set chosen in Step 860 with prominence corresponding to desired force magnitudes 880 — For points located close to each other, merge the corresponding dimples into ridges

FIG. 25

ORTHODONTIC ALIGNERS AND METHODS OF DESIGNING AND FABRICATING ORTHODONTIC ALIGNERS BASED ON TOOTH SHAPE

CROSS-REFERENCE

This application is a continuation of U.S. patent application Ser. No. 17/990,160, filed Nov. 18, 2022, which is a continuation of U.S. patent application Ser. No. 16/433,865, filed Jun. 6, 2019, now U.S. Pat. No. 11,529,215, issued Dec. 20, 2022, which is a continuation of U.S. patent application Ser. No. 14/796,773, filed Jul. 10, 2015, now U.S. Pat. No. 11,571,277, issued Feb. 7, 2023, which is a continuation of U.S. patent application Ser. No. 13/865,091, filed Apr. 17, 2013, now U.S. Pat. No. 9,107,722, issued Aug. 18, 2015, which is a divisional of U.S. patent application Ser. No. 12/346,735, filed Dec. 30, 2008, now U.S. Pat. No. 8,439, 672, issued May 14, 2013, which claims the benefit of U.S. Provisional Patent Application No. 61/024,534, filed Jan. 29, 2008, and of U.S. Provisional Patent Application No. 61/024,526, filed Jan. 29, 2008, the disclosures of which are incorporated, in their entirety, by this reference.

FIELD OF THE INVENTION

The present invention relates to computational orthodontics and dentistry.

BACKGROUND OF THE INVENTION

In orthodontic treatment, a patient's teeth are moved from an initial to a final position using any of a variety of appliances. An appliance exerts force on the teeth by which one or more of them are moved or held in place, as appropriate to the stage of treatment.

The mechanism of the orthodontic movement, as a result of one-to-one correlation between the tooth position and the appliance generation is that the teeth are "squeezed" into the new configuration and held in place, allowing the teeth sufficient time to adapt to the new position, before the process is repeated again as the teeth move progressively along the various treatment stages of a treatment plan.

In the one-to-one correlation between the current treatment state and the subsequent target or n+1 treatment stage, the adaptation of the dental appliance may include interactions between the plastic and the tooth geometry which is suboptimal for achieving n+1 tooth position and is typically not factored into the correlation. This may be the case in particular for larger distances of tooth movement, where the amount of appliance distortion may lead to stretch and stress in the appliance whereby some areas of the aligner are not in close contact with the teeth in critical and/or desirable areas. As a result, the teeth may not be moveable to the desired target position. Moreover, the opposite effect may also exist, where the teeth may be in contact in areas which are counterproductive to reaching the desired or target position.

In addition, the dental attachments are used primarily for changing the geometry of the tooth crown to assure better grip of the dental appliance such as an aligner in the direction of the desired movement. Generally, the attachments operate to provide "bumps" or "undercuts" on the vertical surface of the tooth which otherwise would be difficult for the dental appliance to grip.

Existing approaches to achieve the desired movement of the tooth include fabrication of dental appliances from the planned next or n+1 position and placed over the teeth during the current or n position of the treatment stage. Typically, it is assumed that the forces and torques generated by the deformation of the dental appliance or portions thereof (resulting from the difference in the teeth position used for the dental appliance fabrication and the position of the teeth it has been positioned over) will cause the teeth to move into the planned next position in the treatment stage.

In practice, however, the generated forces and torques may not be oriented in the direction of the intended tooth movement, whether or not dental attachments are used in the treatment. Further, the current tooth movement may be programmed or configured only for the tooth crown, and not factoring into the root of the tooth or other anatomical structures. The root of the tooth or other anatomical structures may hinder the crown movement and render the center of resistance down in the tooth bone socket. Generally, the undesirable torque to the center of resistance as a result of the force on the tooth crown may not be easily counter balanced. Moreover, as the teeth move during the course of the treatment, the deformation of the dental appliance diminishes, rendering the applied forces to diminish as well.

SUMMARY OF THE INVENTION

In one embodiment, method and apparatus including establishing an initial position of a tooth, determining a target position of the tooth in a treatment plan, calculating a movement vector associated with the tooth movement from the initial position to the target position, determining a plurality of components corresponding to the movement vector, and determining a corresponding one or more positions of a respective one or more attachment devices relative to a surface plane of the tooth such that the one or more attachment devices engages with a dental appliance, are provided.

Attachment as used herein may be any form of material that may be attached to the tooth whether preformed, formed using a template or in an amorphous form that is attached to the surface of the tooth. It can be disposed on the tooth surface using an adhesive material, or the adhesive material itself may be disposed on the surface of the tooth as attachment.

These and other features and advantages of the present invention will be understood upon consideration of the following detailed description of the invention and the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1E and 1F show various embodiments of a clusterizer to generate treatment plans;

FIG. 2A is a flowchart of a process of specifying a course of treatment including a subprocess for calculating aligner shapes in accordance with the invention;

FIG. 4 is a flowchart of a subprocess for computing aligner changes;

FIG. 24 is a flowchart illustrating a method of determining if an attachment is required to obtain sufficient active surface area of a tooth;

FIG. 25 is a flowchart of a process for calculating a dental appliance shape;

DETAILED DESCRIPTION OF THE INVENTION

Digital treatment plans are now possible with 3-dimensional orthodontic treatment planning tools such as software from Align Technology, Inc. or other software available from eModels and OrthoCAD, among others. These technologies allow the clinician to use the actual patient's dentition as a starting point for customizing the treatment plan. The software technology available from Align Technology, Inc., uses a patient-specific digital model to plot a treatment plan, and then use a scan of the achieved or actual treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002. The problem with the digital treatment plan and outcome assessment is the abundance of data and the lack of standards and efficient methodology by which to assess "treatment success" at an individual patient level. To analyze the information, a dental data mining system is used.

Figure 1A:
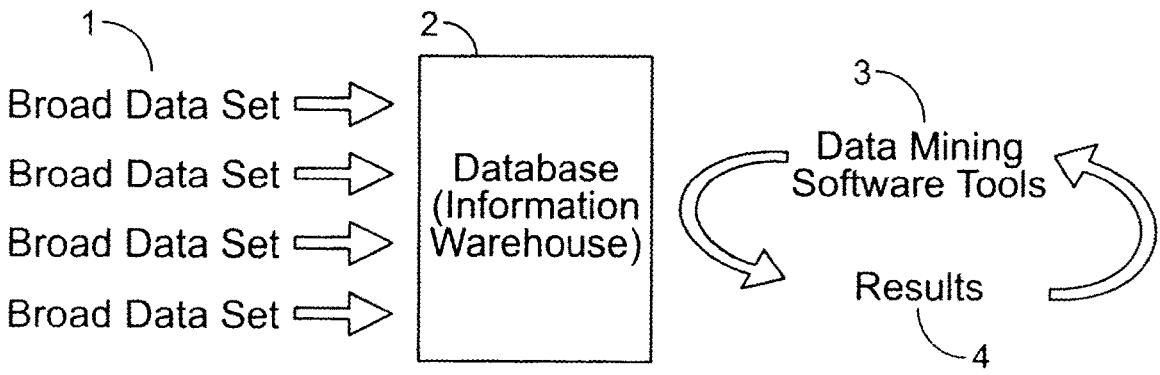
FIG. 1A shows one exemplary dental data mining system.

FIG. 1A shows one exemplary dental data mining system. In this system, dental treatment and outcome data sets 1 are stored in a database or information warehouse 2. The data is extracted by data mining software 3 that generates results 4. The data mining software can interrogate the information captured and/or updated in the database 2 and can generate an output data stream correlating a patient tooth problem with a dental appliance solution. Note that the output of the data mining software can be most advantageously, self-reflexively, fed as a subsequent input to at least the database and the data mining correlation algorithm.

The result of the data mining system of FIG. 1A is used for defining appliance configurations or changes to appliance configurations for incrementally moving teeth. The tooth movements will be those normally associated with orthodontic treatment, including translation in all three orthogonal directions, rotation of the tooth centerline in the two orthogonal directions with rotational axes perpendicular to a vertical centerline ("root angulation" and "torque"), as well as rotation of the tooth centerline in the orthodontic direction with an axis parallel to the vertical centerline ("pure rotation").

In one embodiment, the data mining system captures the 3-D treatment planned movement, the start position and the final achieved dental position. The system compares the outcome to the plan, and the outcome can be achieved using any treatment methodology, including removable appliances as well as fixed appliances, such as orthodontic brackets and wires, or even other dental treatment, such as comparing achieved to plan for orthognathic surgery, periodontics, and restorative, among others.

In one embodiment, a teeth superimposition tool is used to match treatment files of each arch scan. The refinement (subsequent progress) scan is superimposed over the initial one to arrive at a match based upon tooth anatomy and tooth coordinate system. After teeth in the two arches are matched, the superimposition tool asks for a reference in order to relate the upper arch to the lower arch. When the option "statistical filtering" is selected, the superimposition tool measures the amount of movement for each tooth by first eliminating as reference the ones that move (determined by the difference in position between the current stage and the previous one) more than one standard deviation either above or below the mean of movement of all teeth. The remaining teeth are then selected as reference to measure movement of each tooth.

Figure 1B:
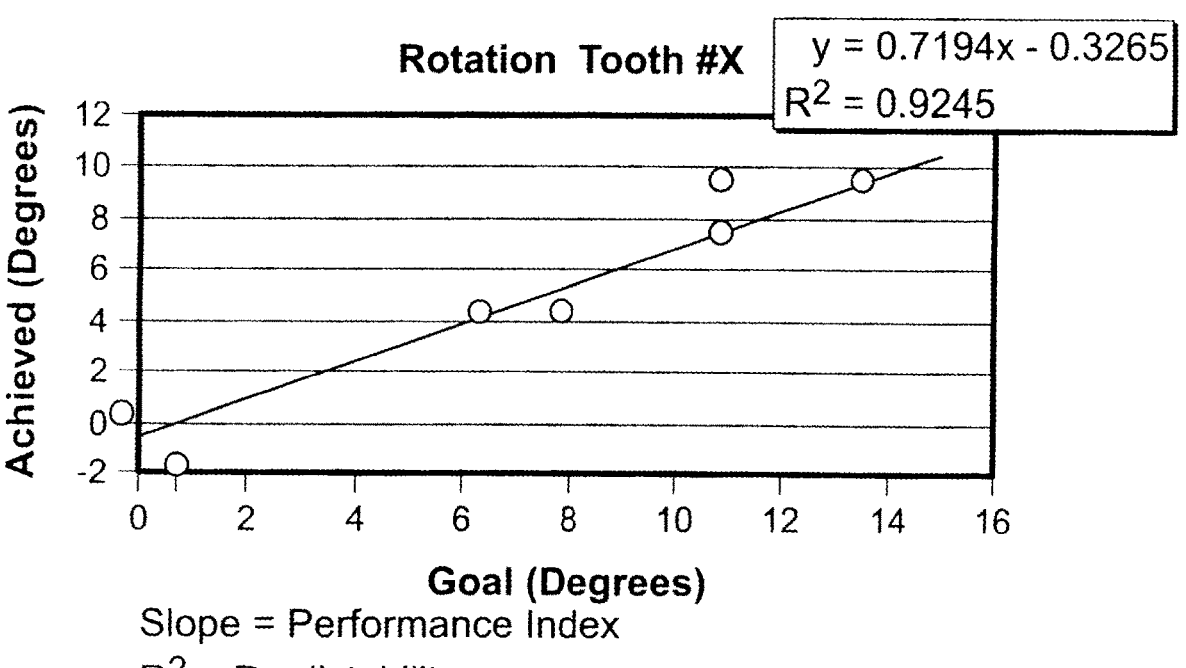
FIG. 1B shows an analysis of the performance of one or more dental appliances.

FIG. 1B shows an analysis of the performance of one or more dental appliances. "Achieved" movement is plotted against "Goal" movement in scatter graphs, and trend lines are generated. Scatter graphs are shown to demonstrate where all "scattered" data points are, and trend lines are generated to show the performance of the dental appliances. In one embodiment, trend lines are selected to be linear (they can be curvilinear); thus, trend lines present as the "best fit" straight lines for all "scattered" data. The performance of the Aligners is represented as the slope of a trend line. The Y axis intercept models the incidental movement that occurs when wearing the Aligners. Predictability is measured by $R^2$ that is obtained from a regression computation of "Achieved" and "Goal" data.

Figures 1C, 1D:
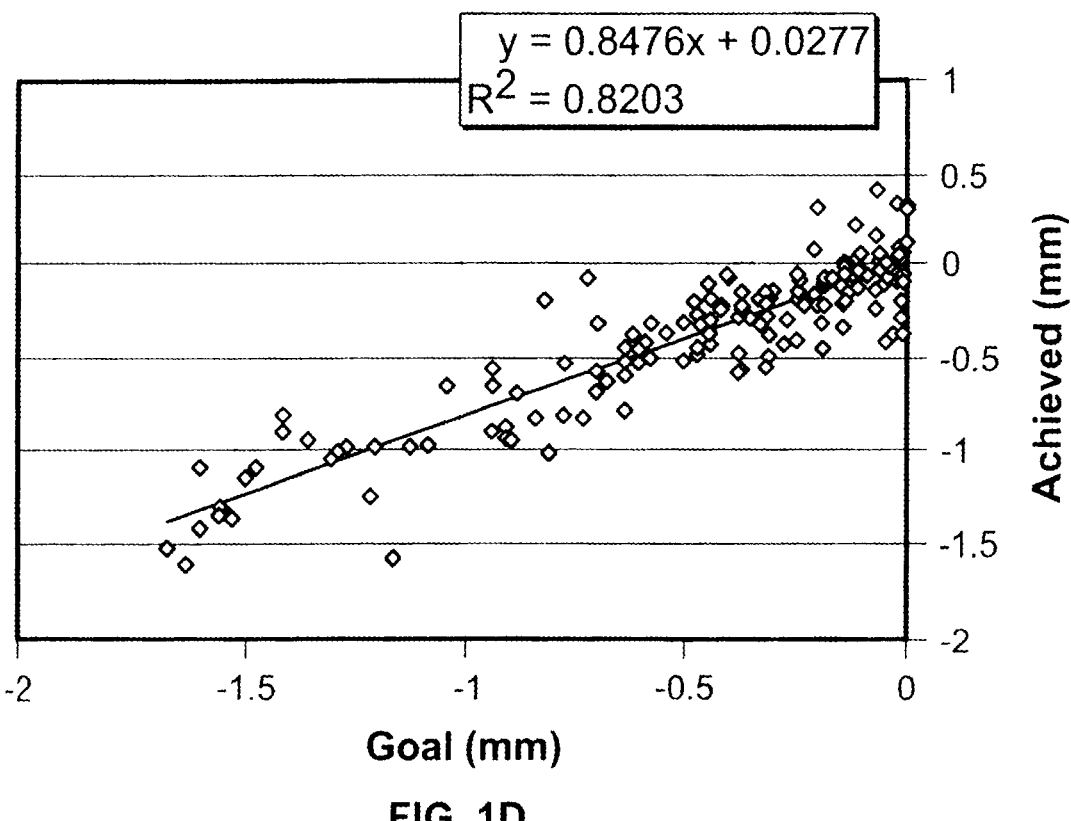
FIG. 1C shows various Movement Type data used in one embodiment of the data mining system.
FIG. 1D shows an analysis of the performance of one or more dental appliances.

FIG. 1C shows various Movement Type data used in one embodiment of the data mining system. Exemplary data sets cover Expansion/Constriction (+/−X Translation), Mesialization/Distalization (+/−Y Translation), Intrusion (−Z Translation), Extrusion (+Z Translation), Tip/Angulation (X Rotation), Torque/Inclination (Y Rotation), and Pure Rotation (Z Rotation).

FIG. 1D shows an analysis of the performance of one or more dental appliances. For the type of motion illustrated by FIG. 1D, the motion achieved is about 85% of targeted motion for that particular set of data.

As illustrated saliently in FIG. 1D, actual tooth movement generally lags targeted tooth movement at many stages. In the case of treatment with sequences of polymer appliances, such lags play an important role in treatment design, because both tooth movement and such negative outcomes as patient discomfort vary positively with the extent of the discrepancies.

In one embodiment, clinical parameters in steps such as 170 (FIG. 2A) and 232 (FIG. 2B) are made more precise by allowing for the statistical deviation of targeted from actual tooth position. For example, a subsequent movement target might be reduced because of a large calculated probability of currently targeted tooth movement not having been achieved adequately, with the result that there is a high probability the subsequent movement stage will need to complete work intended for an earlier stage. Similarly, targeted movement might overshoot desired positions especially in earlier stages so that expected actual movement is better controlled. This embodiment sacrifices the goal of minimizing round trip time in favor of achieving a higher probability of targeted end-stage outcome. This methodology is accomplished within treatment plans specific to clusters of similar patient cases.

Table 1 shows grouping of teeth in one embodiment. The sign convention of tooth movements is indicated in Table 2. Different tooth movements of the selected 60 arches were demonstrated in Table 3 with performance sorted by descending order. The appliance performance can be broken into 4 separate groups: high (79-85%), average (60-68%), below average (52-55%), and inadequate (24-47%). Table 4 shows ranking of movement predictability. Predictability is broken into 3 groups: highly predictable (0.76-0.82), predictable (0.43-0.63) and unpredictable (0.10-0.30). For the particular set of data, for example, the findings are as follows:

Incisor intrusion and anterior intrusion performance are high. The range for incisor intrusion is about 1.7 mm, and for anterior intrusion is about 1.7 mm. These movements are highly predictable.

Canine intrusion, incisor torque, incisor rotation and anterior torque performance are average. The range for canine intrusion is about 1.3 mm, for incisor torque is about 34 degrees, for incisor rotation is about 69 degrees, and for anterior torque is about 34 degrees. These movements are either predictable or highly predictable.

Bicuspid tipping, bicuspid mesialization, molar rotation, and posterior expansion performance are below average. The range for bicuspid mesialization is about 1 millimeter, for bicuspid tipping is about 19 degrees, for molar rotation is about 27 degrees and for posterior expansion is about 2.8 millimeters. Bicuspid tipping and mesialization are unpredictable, whereas the rest are predictable movements.

Anterior and incisor extrusion, round teeth and bicuspid rotation, canine tipping, molar distalization, and posterior torque performance are inadequate. The range of anterior extrusion is about 1.7 millimeters, for incisor extrusion is about 1.5 mm, for round teeth rotation is about 67 degrees, for bicuspid rotation is about 63 degrees, for canine tipping is about 26 degrees, for molar distalization is about 2 millimeters, and for posterior torque is about 43 degrees. All are unpredictable movements except bicuspid rotation which is predictable (but lower in yield in terms of performance).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 1

| Teeth | Studied groups of teeth |
|---|---|
| Incisors | #7, 8, 9, 10, 23, 24, 25, 26 |
| Canines | #6, 11, 22, 27 |
| Bicuspids | #4, 5, 12, 13, 20, 21, 28, 29 |
| Molars | #2, 3, 14, 15, 18, 19, 30, 31 |
| Anteriors | #6, 7, 8, 9, 10, 11, 22, 23, 24, 25, 26, 27 |
| Posteriors | #2, 3, 4, 5, 12, 13, 14, 15, 18, 19, 20, 21, 28, 29, 30, 31 |
| Round | #4, 5, 6, 11, 12, 13, 20, 21, 22, 27, 28, 29 |

7

TABLE 2

Sign convention of tooth movements
Type of Movement

| X translation (Expansion/Constriction) | (−) is lingual | (+) is buccal |
|---|---|---|
| | X rotation (Tipping) | |
| Upper & Lower right quadrants | (−) is distal | (+) is mesial |
| Upper & Lower left quadrants | (−) is mesial | (+) is distal |
| | Y translation (Mesialization/Distalization) | |
| Upper left & Lower right quadrants | (−) is distal | (+) is mesial |
| Upper right & Lower left quadrants | (−) is mesial | (+) is distal |
| Y rotation (Torquing) | (−) is lingual crown | (+) is buccal crown |
| Z translation (Intrusion/Extrusion) | (−) is intrusion | (+) is extrusion |
| Z rotation (Pure Rotation) | (−) is clockwise | (+) is counterclockwise |

TABLE 3

Ranking of Performance Index of movement

| Group | Movement | Model | Performance Index | Side Effect | Predictability |
|---|---|---|---|---|---|
| Incisor | Intrusion | Linear | 85% | 0.03 | 0.82 |
| Anterior | Intrusion | Linear | 79% | 0.03 | 0.76 |
| Canine | Intrusion | Linear | 68% | −0.10 | 0.43 |
| Incisor | Torque | Linear | 67% | 0.21 | 0.63 |
| Anterior | Torque | Linear | 62% | 0.15 | 0.56 |
| Incisor | Rotation | Linear | 61% | −0.09 | 0.76 |
| Bicuspid | Tipping | Linear | 55% | 0.35 | 0.27 |
| Molar | Rotation | Linear | 52% | 0.11 | 0.58 |
| Posterior | Expansion | Linear | 52% | 0.11 | 0.48 |
| Bicuspid | Mesialization | Linear | 52% | 0.00 | 0.30 |
| Bicuspid | Rotation | Linear | 47% | 0.28 | 0.63 |
| Molar | Distalization | Linear | 43% | 0.02 | 0.20 |
| Canine | Tipping | Linear | 42% | 0.10 | 0.28 |
| Posterior | Torque | Linear | 42% | 1.50 | 0.28 |
| Round | Rotation | Linear | 39% | −0.14 | 0.27 |
| Anterior | Extrusion | Linear | 29% | −0.02 | 0.13 |
| Incisor | Extrusion | Linear | 24% | 0.02 | 0.10 |

TABLE 4

Ranking of movement predictability

| Group | Movement | Model | Performance Index | Side Effect | Predictability |
|---|---|---|---|---|---|
| Incisor | Intrusion | Linear | 85% | 0.03 | 0.82 |
| Anterior | Intrusion | Linear | 79% | 0.03 | 0.76 |
| Incisor | Rotation | Linear | 61% | −0.09 | 0.76 |
| Incisor | Torque | Linear | 67% | 0.21 | 0.63 |
| Bicuspid | Rotation | Linear | 47% | 0.28 | 0.63 |
| Molar | Rotation | Linear | 52% | 0.11 | 0.58 |
| Anterior | Torque | Linear | 62% | 0.15 | 0.56 |
| Posterior | Expansion | Linear | 52% | 0.11 | 0.48 |
| Canine | Intrusion | Linear | 68% | −0.10 | 0.43 |
| Bicuspid | Mesialization | Linear | 52% | 0.00 | 0.30 |
| Canine | Tipping | Linear | 42% | 0.10 | 0.28 |
| Posterior | Torque | Linear | 42% | 1.50 | 0.28 |
| Bicuspid | Tipping | Linear | 55% | 0.35 | 0.27 |
| Round | Rotation | Linear | 39% | −0.14 | 0.27 |
| Molar | Distalization | Linear | 43% | 0.02 | 0.20 |
| Anterior | Extrusion | Linear | 29% | −0.02 | 0.13 |
| Incisor | Extrusion | Linear | 24% | 0.02 | 0.10 |

8

In one embodiment, data driven analyzers may be applied. These data driven analyzers may incorporate a number of models such as parametric statistical models, non-parametric statistical models, clustering models, nearest neighbor models, regression methods, and engineered (artificial) neural networks. Prior to operation, data driven analyzers or models are built using one or more training sessions. The data used to build the analyzer or model in these sessions are typically referred to as training data. As data driven analyzers are developed by examining only training examples, the selection of the training data can significantly effect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In one embodiment, the data mining software 3 (FIG. 1A) can be a "spider" or "crawler" to grab data on the database 2 (FIG. 1A) for indexing. In one embodiment, clustering operations are performed to detect patterns in the data. In another embodiment, a neural network is used to recognize each pattern as the neural network is quite robust at recognizing dental treatment patterns. Once the treatment features have been characterized, the neural network then compares the input dental information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible paths of M "frames" through N points, subject to specified costs for making transitions from any point i to any given frame k to any point j at the next frame k+1. Because the best path from the current point to the next point is independent of what happens beyond that point, the minimum total cost [i(k), j(k+1)] of a path through i(k) ending at j(k+1) is the cost of the transition itself plus the cost of the minimum path to i(k). Preferably, the values of the predecessor paths can be kept in an M×N array, and the accumulated cost kept in a 2×N array to contain the accumulated costs of the possible immediately preceding column and the current column. However, this method requires significant computing resources.

Dynamic programming requires a tremendous amount of computation. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of dental treatment information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable.

In the preferred embodiment, the Markov model is used to model probabilities for sequences of treatment observations. The transitions between states are represented by a transition matrix $A=[a(i,j)]$. Each $a(i,j)$ term of the transition matrix is the probability of making a transition to state j given that the model is in state i. The output symbol probability of the model is represented by a set of functions $B=[b(j)]$, where the $b(j)$ term of the output symbol matrix is the function that when evaluated on a specified value O(t) returns the probability of outputting observation O(t), given that the model is in state j. The first state is always constrained to be the initial state for the first time frame of the Markov chain, only a prescribed set of left to right state transitions are possible. A predetermined final state is defined from which transitions to other states cannot occur.

In one embodiment, transitions are restricted to reentry of a state or entry to one of the next two states. Such transitions are defined in the model as transition probabilities. For example, a treatment pattern currently having a frame of feature signals in state 2 has a probability of reentering state 2 of $a(2,2)$, a probability $a(2,3)$ of entering state 3 and a probability of $a(2,4)=1-a(2,2)-a(2,3)$ of entering state 4. The probability $a(2,1)$ of entering state 1 or the probability $a(2,5)$ of entering state 5 is zero and the sum of the probabilities $a(2,1)$ through $a(2,5)$ is one. Although the preferred embodiment restricts the flow graphs to the present state or to the next two states, one skilled in the art can build an HMM model with more flexible transition restrictions, although the sum of all the probabilities of transitioning from any state must still add up to one.

In each state j of the model, the current feature frame may be identified with one of a set of predefined output symbols or may be labeled probabilistically. In this case, the output symbol probability $b(j)$ (O(t)) corresponds to the probability assigned by the model that the feature frame symbol is O(t). The model arrangement is a matrix $A=[a(i,j)]$ of transition probabilities and a technique of computing $B=[b(j)(O(t))]$.

In one embodiment, the Markov model is formed for a reference pattern from a plurality of sequences of training patterns and the output symbol probabilities are multivariate Gaussian function probability densities. The dental treatment information traverses through the feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

The HMM template has a number of states, each having a discrete value. However, as treatment pattern features may have a dynamic pattern in contrast to a single value, the addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output neurons, which output neurons correspond one-to one with internal states of the HMM. However, each output has transition probabilities to itself or to other outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The output streams or results 4 of FIG. 1A are used as feedback in improving dental appliance design and/or usage by doctors. For example, the data mining results can be used to evaluate performance based on staging approaches, to compare appliance performance indices based on treatment approaches, and to evaluate performance comparing different attachment shapes and positions on teeth.

The ability to study tooth-specific efficacy and product performance for large clusters of treatment outcomes enables statistically significant comparisons to be made between two or more populations of cases. In the event that the two clusters studied contain differences in treatment approach, appliance design, or manufacturing protocol, the differences seen in the performance of the product as exhibited by the data output, can be attributed to the approach, design, or manufacturing protocol. The end result is a feedback mechanism that enables either the clinician or the manufacturer the ability to optimize the product design and usage based on performance data from a significantly large sample size using objective measurable data.

The theory of orthodontic treatment is not universally agreed upon, and actual treatment and outcomes are subject to additional uncertainties of measurement of patient variables, of relationships to unmeasured patient variables, as well as of varying patient compliance. As a result, different clinicians might prefer different treatment plans for a single patient. Thus, a single treatment plan may not be accepted by every clinician since there is no universally accepted "correct" treatment plan.

The next few embodiments allow greater clinician satisfaction and greater patient satisfaction by tailoring treatment parameters to preferences of clinicians. The system detects differences in treatment preferences by statistical observation of the treatment histories of clinicians. For example, clinicians vary in how likely they would be to perform bicuspid extraction in cases with comparable crowding. Even when there is not a sufficient record of past treatments for a given clinician, clustering may be performed on other predictor variables such as geographical location, variables related to training, or size and nature of practice, to observe statistically significant differences in treatment parameters.

Data mining can discover statistically significant patterns of different treatment outcomes achieved by different clinicians for comparable patients. For example, patient cases clustered together might have systematically fewer complications with one clinician as compared to another. Such a difference detected by the data mining tool might be used as a flag for feedback to the more poorly performing clinician as well as a flag for solicitation of treatment differences used by the better performing clinician.

In one embodiment, clustering techniques are used with previously completed cases to categorize treatment complications and outcomes. Probability models of risk are then built within each cluster. New cases are then allocated to the same clusters based on similarity of pre-treatment variables. The risks within each cluster of patients with completed treatments are then used with new cases to predict treatment outcomes and risks of complications. High-risk patients are then flagged for special attention, possibly including additional steps in treatment plan or additional clinical intervention.

In another embodiment, practitioners are clustered into groups by observed clinician treatment preferences, and treatment parameters are adjusted within each group to coincide more closely with observed treatment preferences. Practitioners without observed histories are then assigned to groups based on similarity of known variables to those within clusters with known treatment histories.

FIG. 1E shows an exemplary process for clusterizing practices. First, the process clusterizes treatment practice based on clinician treatment history such as treatment preferences, outcomes, and demographic and practice variables (20). Next, the system models preferred clinical constraints within each cluster (22). Next, the system assigns clinicians without treatment history to clusters in 20 based on demographic and practice variables (24). In one embodiment, the system performs process 100 (see FIG. 2A) separately within each cluster, using cluster-specific clinical constraints (26). Additionally, the system updates clusters and cluster assignments as new treatment and outcome data arrives (28).

FIG. 1F shows another embodiment of a data mining system to generate proposed treatments. First, the system identifies/clusterizes patient histories having detailed follow-up (such as multiple high-resolution scans), based on detailed follow-up data, diagnosis, treatment parameters and outcomes, and demographic variables (40). Within each cluster, the system models discrepancies between intended position and actual positions obtained from follow-up data (42). Further, within each cluster, the system models risk for special undesirable outcomes (44). At a second tier of clustering, patient histories with less detailed follow-up data are clusterized based on available variables. The second-tier clustering is partial enough that each of the larger number of second tier clusters can either be assigned to clusters calculated in 40 or else considered a new cluster (46). The system refines step 42 models with additional records from step 46 clusters (48). It can also refine step 44 models with additional records from step 48 clusters (50). At a third tier of clustering, the system then assigns new patients to step 46 clusters based on diagnosis, demographic, and initial physical (52). Within each step 52 cluster, the system models expected discrepancies between intended position and actual positions (54). From step 54, the system uses revised expected position information where relevant (including 232 and 250, FIG. 2B) (67). Additionally, within each step 52 cluster, the system models risk for undesirable outcomes (56). From step 56, the system also flags cases that require special attention and clinical constraints (as in 204 and 160, FIGS. 2B and 2A) (69). The process then customizes treatment plan to each step 52 cluster (58). Next, the system iteratively collects data (61) and loops back to identify/clusterize patient histories (40). Additionally, clusters can be revised and reassigned (63). The system also continually identifies clusters without good representation for additional follow-up analysis (65).

In clinical treatment settings, it is not cost-effective to obtain or process the full high-resolution data possible at every stage of tooth movement. For example:

Patients may use several appliances between visits to clinicians.

A given patient may submit only one set of tooth impressions.

Radiation concerns may limit the number of CT or X-Ray scans used.

Clinicians generally do not have the time to report detailed spatial information on each tooth at each visit.

Due to these and other limitations, treatment planning is necessarily made based on partial information.

In one embodiment, missing information is approximated substantially by matching predictive characteristics between patients and a representative sample for which detailed follow-up information is collected. In this case, patients are flagged based on poorly anticipated treatment outcomes for requests for follow-up information, such as collection and analysis of additional sets of tooth impressions. Resulting information is then used to refine patient clusters and treatment of patients later assigned to the clusters.

In general, patient data is scanned, and the data is analyzed using the data mining system described above. A treatment plan is proposed by the system for the dental practitioner to approve. The dental practitioner can accept or request modifications to the treatment plan. Once the treatment plan is approved, manufacturing of appliance(s) can begin.

FIG. 2A illustrates the general flow of an exemplary process 100 for defining and generating repositioning appliances for orthodontic treatment of a patient. The process 100 includes the methods, and is suitable for the apparatus, of the present invention, as will be described. The computational steps of the process are advantageously implemented as computer program modules for execution on one or more conventional digital computers.

As an initial step, a mold or a scan of patient's teeth or mouth tissue is acquired (110). This step generally involves taking casts of the patient's teeth and gums and may, in addition or alternately, involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the tissue constituents from each other (step 120). In particular, in this step, data structures that digitally represent individual tooth crowns are produced. Advantageously, digital models of entire teeth are produced, including measured or extrapolated hidden surfaces and root structures as well as surrounding bone and soft tissue.

The desired final position of the teeth—that is, the desired and intended end result of orthodontic treatment—can be received from a clinician in the form of a prescription, can be calculated from basic orthodontic principles, or can be extrapolated computationally from a clinical prescription (step 130). With a specification of the desired final positions of the teeth and a digital representation of the teeth themselves, the final position and surface geometry of each tooth can be specified (step 140) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a final position for each tooth, the process next defines a tooth path for the motion of each tooth. In one embodiment, the tooth paths are optimized in the aggregate so that the teeth are moved in the quickest fashion with the least amount of round-tripping to bring the teeth from their initial positions to their desired final positions. (Round-tripping is any motion of a tooth in any direction other than directly toward the desired final position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (step 170, described later), which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths (step 150) can recalculate the paths or the affected subpaths.

At various stages of the process, and in particular after the segmented paths have been defined, the process can, and generally will, interact with a clinician responsible for the treatment of the patient (step 160). Clinician interaction can be implemented using a client process programmed to receive tooth positions and models, as well as path information from a server computer or process in which other steps of process 100 are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the subprocess of defining segmented paths (step 150) is performed again.

The segmented tooth paths and associated tooth position data are used to calculate clinically acceptable appliance configurations (or successive changes in appliance configuration) that will move the teeth on the defined treatment path in the steps specified by the path segments (step 170). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (step 160). The operation of a process step 200 implementing this step will be described more fully below.

Having calculated appliance definitions, the process 100 can proceed to the manufacturing step (step 180) in which appliances defined by the process are manufactured, or electronic or printed information is produced that can be used by a manual or automated process to define appliance configurations or changes to appliance configurations.

Figure 2B:
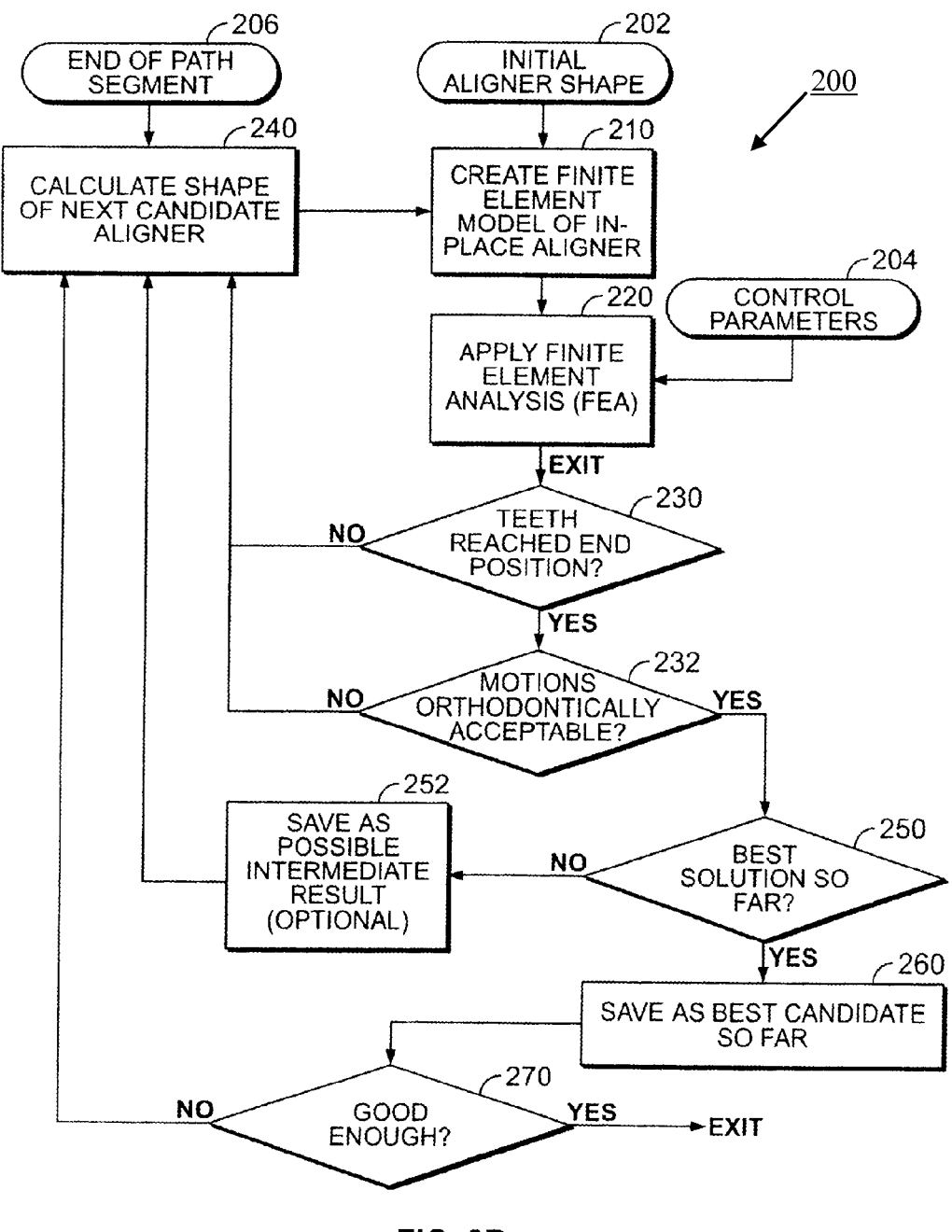
FIG. 2B is a flowchart of a process for calculating aligner shapes.

FIG. 2B illustrates a process 200 implementing the appliance-calculation step (FIG. 2A, step 170) for polymeric shell aligners of the kind described in above-mentioned U.S. Pat. No. 5,975,893. Inputs to the process include an initial aligner shape 202, various control parameters 204, and a desired end configuration for the teeth at the end of the current treatment path segment 206. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth (step 210). Next, the process applies a finite element analysis to the composite finite element model of aligner, teeth and tissue (step 220). The analysis runs until an exit condition is reached, at which time the process evaluates whether the teeth have reached the desired end position for the current path segment, or a position sufficiently close to the desired end position (step 230). If an acceptable end position is not reached by the teeth, the process calculates a new candidate aligner shape (step 240). If an acceptable end position is reached, the motions of the teeth calculated by the finite elements analysis are evaluated to determine whether they are orthodontically acceptable (step 232). If they are not, the process also proceeds to calculate a new candidate aligner shape (step 240). If the motions are orthodontically acceptable and the teeth have reached an acceptable position, the current aligner shape is compared to the previously calculated aligner shapes. If the current shape is the best solution so far (decision step 250), it is saved as the best candidate so far (step 260). If not, it is saved in an optional step as a possible intermediate result (step 252). If the current aligner shape is the best candidate so far, the process determines whether it is good enough to be accepted (decision step 270). If it is, the process exits. Otherwise, the process continues and calculates another candidate shape (step 240) for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from MacNeal-Schwendler Corporation of Los Angeles, California.

Figure 3:
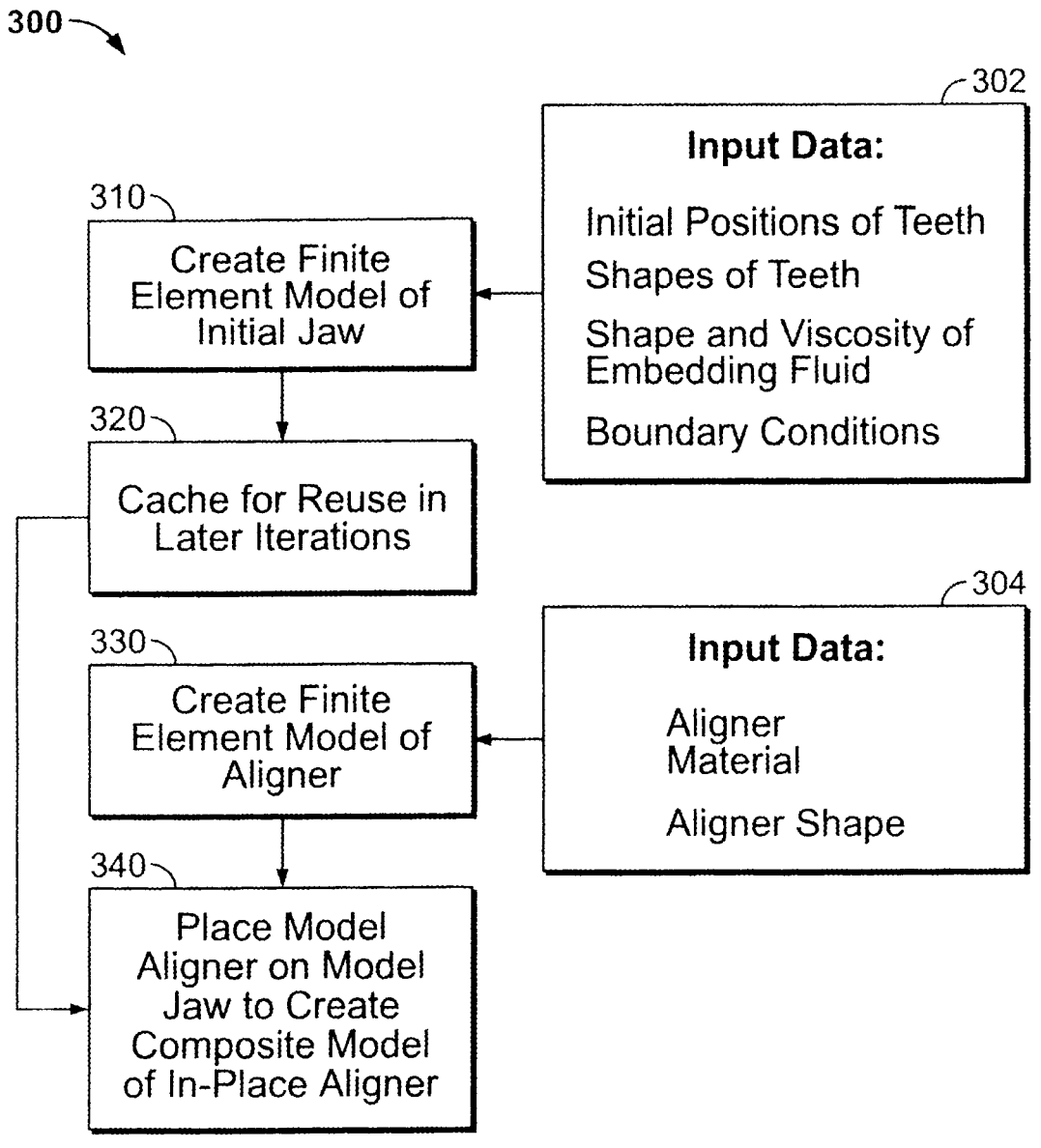
FIG. 3 is a flowchart of a subprocess for creating finite element models.

FIG. 3 shows a process 300 of creating a finite element model that can be used to perform step 210 of the process 200 (FIG. 2). Input to the model creation process 300 includes input data 302 describing the teeth and tissues and input data 304 describing the aligner. The input data describing the teeth 302 include the digital models of the teeth; digital models of rigid tissue structures, if available; shape and viscosity specifications for a highly viscous fluid modeling the substrate tissue in which the teeth are embedded and to which the teeth are connected, in the absence of specific models of those tissues; and boundary conditions specifying the immovable boundaries of the model elements. In one implementation, the model elements include only models of the teeth, a model of a highly viscous embedding substrate fluid, and boundary conditions that define, in effect, a rigid container in which the modeled fluid is held. Note that fluid characteristics may differ by patient clusters, for example as a function of age.

A finite element model of the initial configuration of the teeth and tissue is created (step 310) and optionally cached for reuse in later iterations of the process (step 320). As was done with the teeth and tissue, a finite element model is created of the polymeric shell aligner (step 330). The input data for this model includes data specifying the material of which the aligner is made and the shape of the aligner (data input 304).

The model aligner is then computationally manipulated to place it over the modeled teeth in the model jaw to create a composite model of an in-place aligner (step 340). Optionally, the forces required to deform the aligner to fit over the teeth, including any hardware attached to the teeth, are computed and used as a figure of merit in measuring the acceptability of the particular aligner configuration. Optionally, the tooth positions used are as estimated from a probabilistic model based on prior treatment steps and other patient information. In a simpler alternative, however, the aligner deformation is modeled by applying enough force to its insides to make it large enough to fit over the teeth, placing the model aligner over the model teeth in the composite model, setting the conditions of the model teeth and tissue to be infinitely rigid, and allowing the model aligner to relax into position over the fixed teeth. The surfaces of the aligner and the teeth are modeled to interact without friction at this stage, so that the aligner model achieves the correct initial configuration over the model teeth before finite element analysis is begun to find a solution to the composite model and compute the movement of the teeth under the influence of the distorted aligner.

FIG. 4 shows a process 400 for calculating the shape of a next aligner that can be used in the aligner calculations, step 240 of process 200 (FIG. 2B). A variety of inputs are used to calculate the next candidate aligner shape. These include inputs 402 of data generated by the finite element analysis solution of the composite model and data 404 defined by the current tooth path. The data 402 derived from the finite element analysis includes the amount of real elapsed time over which the simulated repositioning of the teeth took place; the actual end tooth positions calculated by the analysis; the maximum linear and torsional force applied to each tooth; the maximum linear and angular velocity of each tooth. From the input path information, the input data 404 includes the initial tooth positions for the current path segment, the desired tooth positions at the end of the current path segment, the maximum allowable displacement velocity for each tooth, and the maximum allowable force of each kind for each tooth.

If a previously evaluated aligner was found to violate one or more constraints, additional input data 406 can optionally be used by the process 400. This data 406 can include information identifying the constraints violated by, and any identified suboptimal performance of, the previously evaluated aligner. Additionally, input data 408 relating to constraints violated by, and suboptimal performance of previous dental devices can be used by the process 400.

Having received the initial input data (step 420), the process iterates over the movable teeth in the model. (Some of the teeth may be identified as, and constrained to be, immobile.) If the end position and dynamics of motion of the currently selected tooth by the previously selected aligner is acceptable ("yes" branch of decision step 440), the process continues by selecting for consideration a next tooth (step 430) until all teeth have been considered ("done" branch from step 430 to step 470). Otherwise ("no" branch from step 440), a change in the aligner is calculated in the region of the currently selected tooth (step 450). The process then moves back to select the next current tooth (step 430) as has been described.

When all of the teeth have been considered, the aggregate changes made to the aligner are evaluated against previously defined constraints (step 470), examples of which have already been mentioned. Constraints can be defined with reference to a variety of further considerations, such as manufacturability. For example, constraints can be defined to set a maximum or minimum thickness of the aligner material, or to set a maximum or minimum coverage of the aligner over the crowns of the teeth. If the aligner constraints are satisfied, the changes are applied to define a new aligner shape (step 490). Otherwise, the changes to the aligner are revised to satisfy the constraints (step 480), and the revised changes are applied to define the new aligner shape (step 490).

Figure 5A:
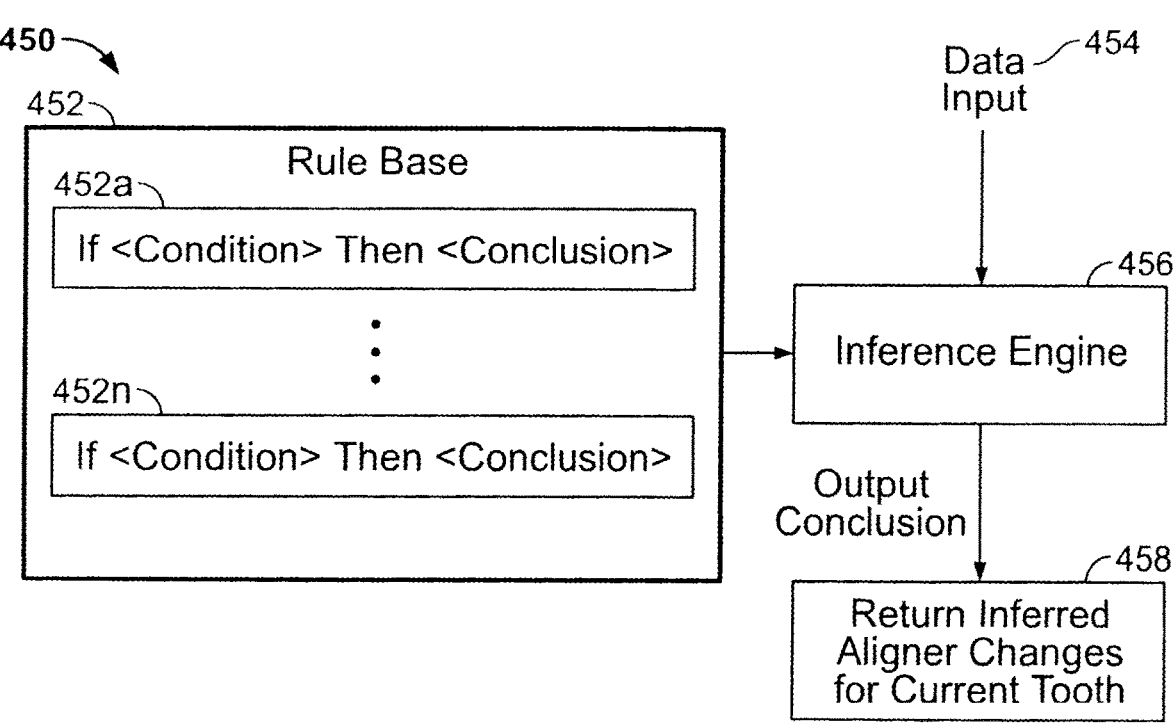
FIG. 5A is a flowchart of a subprocess for calculating changes in aligner shape.

FIG. 5A illustrates one implementation of the step of computing an aligner change in a region of a current tooth (step 450). In this implementation, a rule-based inference engine 456 is used to process the input data previously described (input 454) and a set of rules 452a-452n in a rule base of rules 452. The inference engine 456 and the rules 452 define a production system which, when applied to the factual input data, produces a set of output conclusions that specify the changes to be made to the aligner in the region of the current tooth (output 458).

Rules 452a . . . 452n have the conventional two-part form: an if-part defining a condition and a then-part defining a conclusion or action that is asserted if the condition is satisfied. Conditions can be simple or they can be complex conjunctions or disjunctions of multiple assertions. An exemplary set of rules, which defines changes to be made to the aligner, includes the following: if the motion of the tooth is too fast, add driving material to the aligner opposite the desired direction of motion; if the motion of the tooth is too slow, add driving material to overcorrect the position of the tooth; if the tooth is too far short of the desired end position, add material to overcorrect; if the tooth has been moved too far past the desired end position, add material to stiffen the aligner where the tooth moves to meet it; if a maximum amount of driving material has been added, add material to overcorrect the repositioning of the tooth and do not add driving material; if the motion of the tooth is in a direction other than the desired direction, remove and add material so as to redirect the tooth.

Figure 5B:
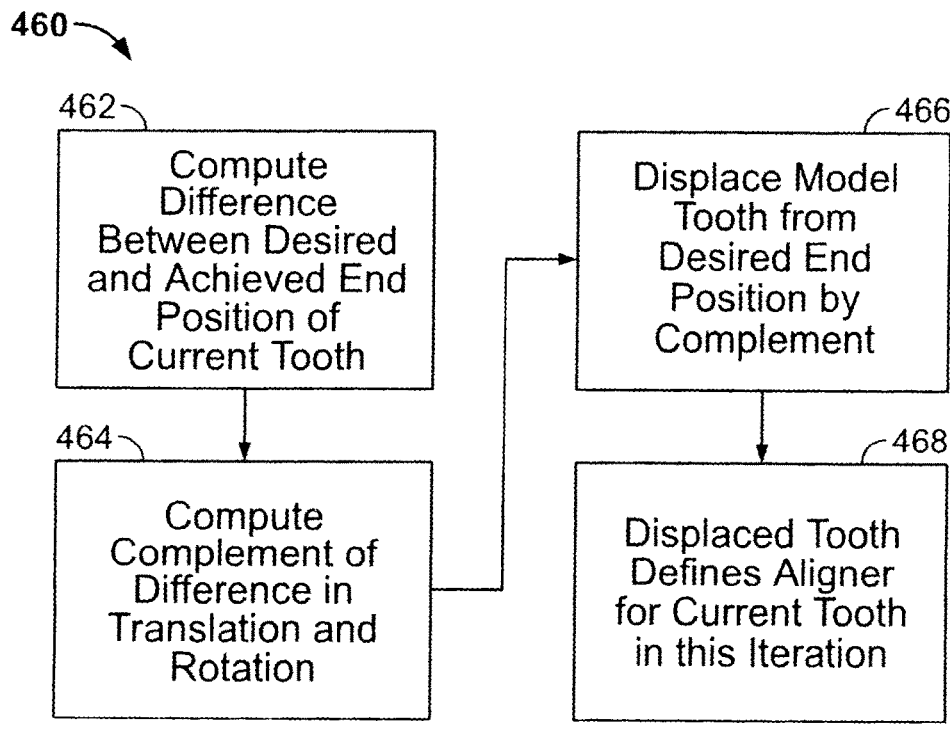
FIG. 5B is a flowchart of a subprocess for calculating changes in aligner shape.
Figure 5C:
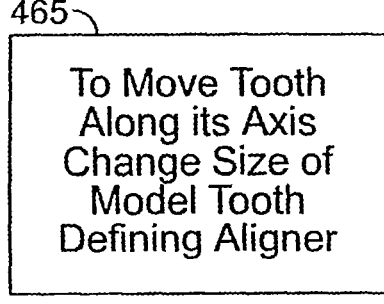
FIG. 5C is a flowchart of a subprocess for calculating changes in aligner shape.

In an alternative embodiment, illustrated in FIGS. 5B and 5C, an absolute configuration of the aligner is computed, rather than an incremental difference. As shown in FIG. 5B, a process 460 computes an absolute configuration for an aligner in a region of a current tooth. Using input data that has already been described, the process computes the difference between the desired end position and the achieved end position of the current tooth (462). Using the intersection of the tooth center line with the level of the gum tissue as the point of reference, the process computes the complement of the difference in all six degrees of freedom of motion, namely three degrees of translation and three degrees of rotation (step 464). Next, the model tooth is displaced from its desired end position by the amounts of the complement differences (step 466), which is illustrated in FIG. 5B.

Figure 5D:
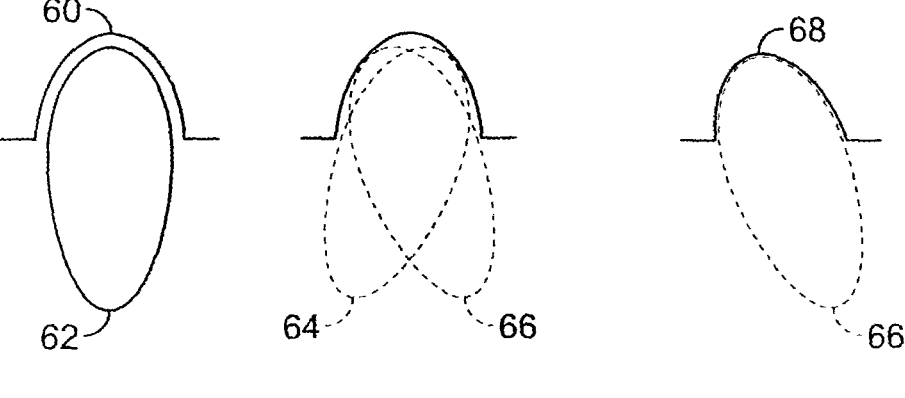
FIG. 5D is a schematic illustrating the operation of the subprocess of FIG. 5B.

FIG. 5D shows a planar view of an illustrative model aligner 60 over an illustrative model tooth 62. The tooth is in its desired end position and the aligner shape is defined by the tooth in this end position. The actual motion of the tooth calculated by the finite element analysis is illustrated as placing the tooth in position 64 rather than in the desired position 62. A complement of the computed end position is illustrated as position 66. The next step of process 460 (FIG. 5B) defines the aligner in the region of the current tooth in this iteration of the process by the position of the displaced model tooth (step 468) calculated in the preceding step (466). This computed aligner configuration in the region of the current tooth is illustrated in FIG. 5D as shape 68 which is defined by the repositioned model tooth in position 66.

A further step in process 460, which can also be implemented as a rule 452 (FIG. 5A), is shown in FIG. 5C. To move the current tooth in the direction of its central axis, the size of the model tooth defining that region of the aligner, or the amount of room allowed in the aligner for the tooth, is made smaller in the area away from which the process has decided to move the tooth (step 465).

Figure 6:
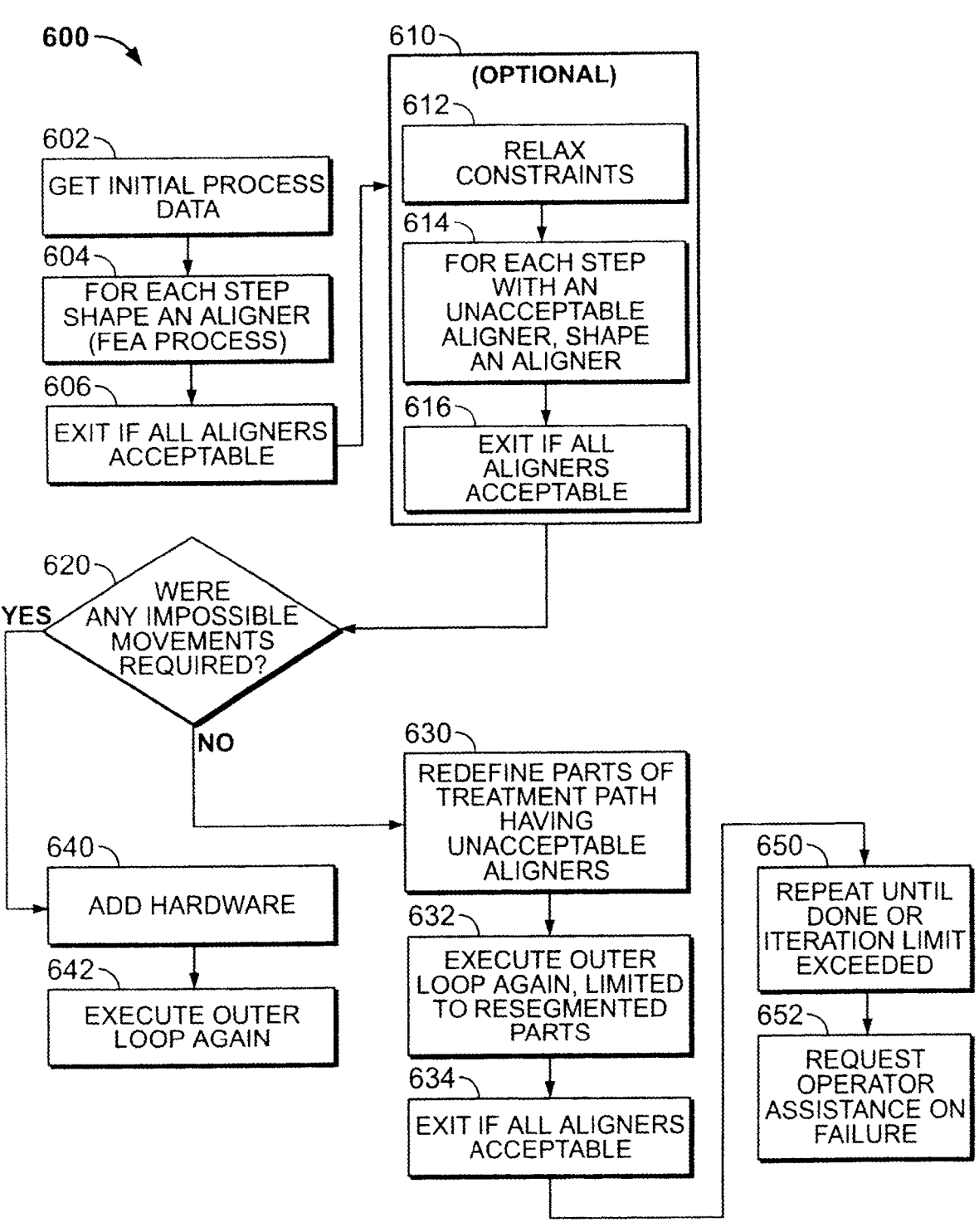
FIG. 6 is a flowchart of a process for computing shapes for sets of aligners.

As shown in FIG. 6, the process 200 (FIG. 2B) of computing the shape for an aligner for a step in a treatment path is one step in a process 600 of computing the shapes of a series of aligners. This process 600 begins with an initialization step 602 in which initial data, control and constraint values are obtained.

When an aligner configuration has been found for each step or segment of the treatment path (step 604), the process 600 determines whether all of the aligners are acceptable (step 606). If they are, the process is complete. Otherwise, the process optionally undertakes a set of steps 610 in an attempt to calculate a set of acceptable aligners. First, one or more of the constraints on the aligners is relaxed (step 612). Then, for each path segment with an unacceptable aligner, the process 200 (FIG. 2B) of shaping an aligner is performed with the new constraints (step 614). If all the aligners are now acceptable, the process 600 exits (step 616).

Aligners may be unacceptable for a variety of reasons, some of which are handled by the process. For example, if any impossible movements were required (decision step 620), that is, if the shape calculation process 200 (FIG. 2B) was required to effect a motion for which no rule or adjustment was available, the process 600 proceeds to execute a module that calculates the configuration of a hardware attachment to the subject tooth to which forces can be applied to effect the required motion (step 640). Because adding hardware can have an effect that is more than local, when hardware is added to the model, the outer loop of the process 600 is executed again (step 642).

If no impossible movements were required ("no" branch from step 620), the process transfers control to a path definition process (such as step 150, FIG. 2A) to redefine those parts of the treatment path having unacceptable aligners (step 630). This step can include both changing the increments of tooth motion, i.e., changing the segmentation, on the treatment path, changing the path followed by one or more teeth in the treatment path, or both. After the treatment path has been redefined, the outer loop of the process is executed again (step 632). The recalculation is advanta-geously limited to recalculating only those aligners on the redefined portions of the treatment path. If all the aligners are now acceptable, the process exits (step 634). If unacceptable aligners still remain, the process can be repeated until an acceptable set of aligners is found, or an iteration limit is exceeded (step 650). At this point, as well as at other points in the processes that are described in this specification, such as at the computation of additional hardware (step 640), the process can interact with a human operator, such as a clinician or technician, to request assistance (step 652). Assistance that an operator provides can include defining or selecting suitable attachments to be attached to a tooth or a bone, defining an added elastic element to provide a needed force for one or more segments of the treatment path, suggesting an alteration to the treatment path, either in the motion path of a tooth or in the segmentation of the treatment path, and approving a deviation from or relaxation of an operative constraint.

As was mentioned above, the process 600 is defined and parameterized by various items of input data (step 602). In one implementation, this initializing and defining data includes the following items: an iteration limit for the outer loop of the overall process; specification of figures of merit that are calculated to determine whether an aligner is good enough (see FIG. 2B, step 270); a specification of the aligner material; a specification of the constraints that the shape or configuration of an aligner must satisfy to be acceptable; a specification of the forces and positioning motions and velocities that are orthodontically acceptable; an initial treatment path, which includes the motion path for each tooth and a segmentation of the treatment path into segments, each segment to be accomplished by one aligner; a specification of the shapes and positions of any anchors installed on the teeth or otherwise; and a specification of a model for the jaw bone and other tissues in or on which the teeth are situated (in the implementation being described, this model consists of a model of a viscous substrate fluid in which the teeth are embedded and which has boundary conditions that essentially define a container for the fluid).

Figure 7:
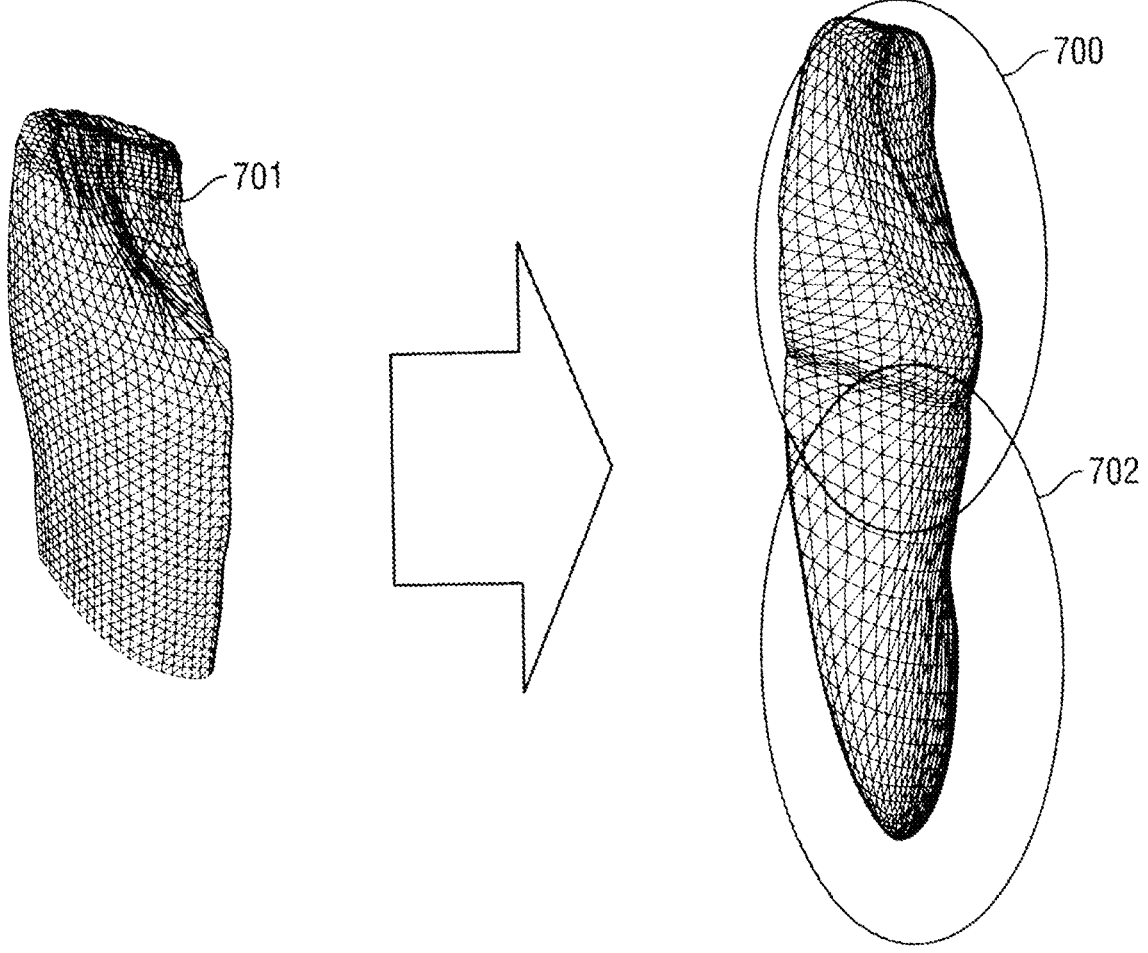
FIG. 7 is an exemplary diagram of a statistical root model.

FIG. 7 is an exemplary diagram of a statistical root model. As shown therein, using the scanning processes described above, a scanned upper portion 701 of a tooth is identified. The scanned upper portion, including the crown, is then supplemented with a modeled 3D root. The 3D model of the root can be statistically modeled. The 3D model of the root 702 and the 3D model of the upper portion 700 together form a complete 3D model of a tooth.

Figure 8:
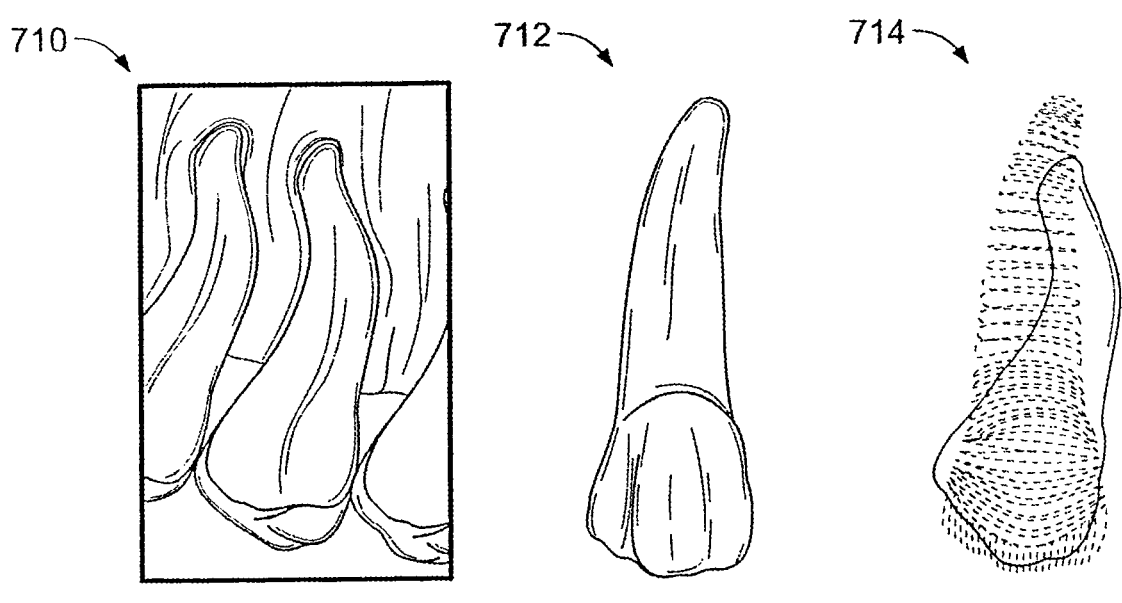
FIG. 8 shows exemplary diagrams of root modeling.

FIG. 8 shows exemplary diagrams of root modeling, as enhanced using additional dental information. In FIG. 8, the additional dental information is X-ray information. An X-ray image 710 of teeth is scanned to provide a 2D view of the complete tooth shapes. An outline of a target tooth is identified in the X-Ray image. The model 712 as developed in FIG. 7 is modified in accordance with the additional information. In one embodiment, the tooth model of FIG. 7 is morphed to form a new model 714 that conforms with the X-ray data.

Figure 9:
FIG. 9 show exemplary diagrams of CT scan of teeth.

FIG. 9 shows an exemplary diagram of a CT scan of teeth. In this embodiment, the roots are derived directly from a high-resolution CBCT scan of the patient. Scanned roots can then be applied to crowns derived from an impression or used with the existing crowns extracted from Cone Beam Computed Tomography (CBCT) data. A CBCT single scan gives 3D data and multiple forms of X-ray-like data. PVS impressions are avoided.

In one embodiment, a cone beam x-ray source and a 2D area detector scans the patient's dental anatomy, preferably over a 360-degree angular range and along its entire length, by any one of various methods wherein the position of the area detector is fixed relative to the source, and relative rotational and translational movement between the source and object provides the scanning (irradiation of the object by radiation energy). As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

Figure 10:
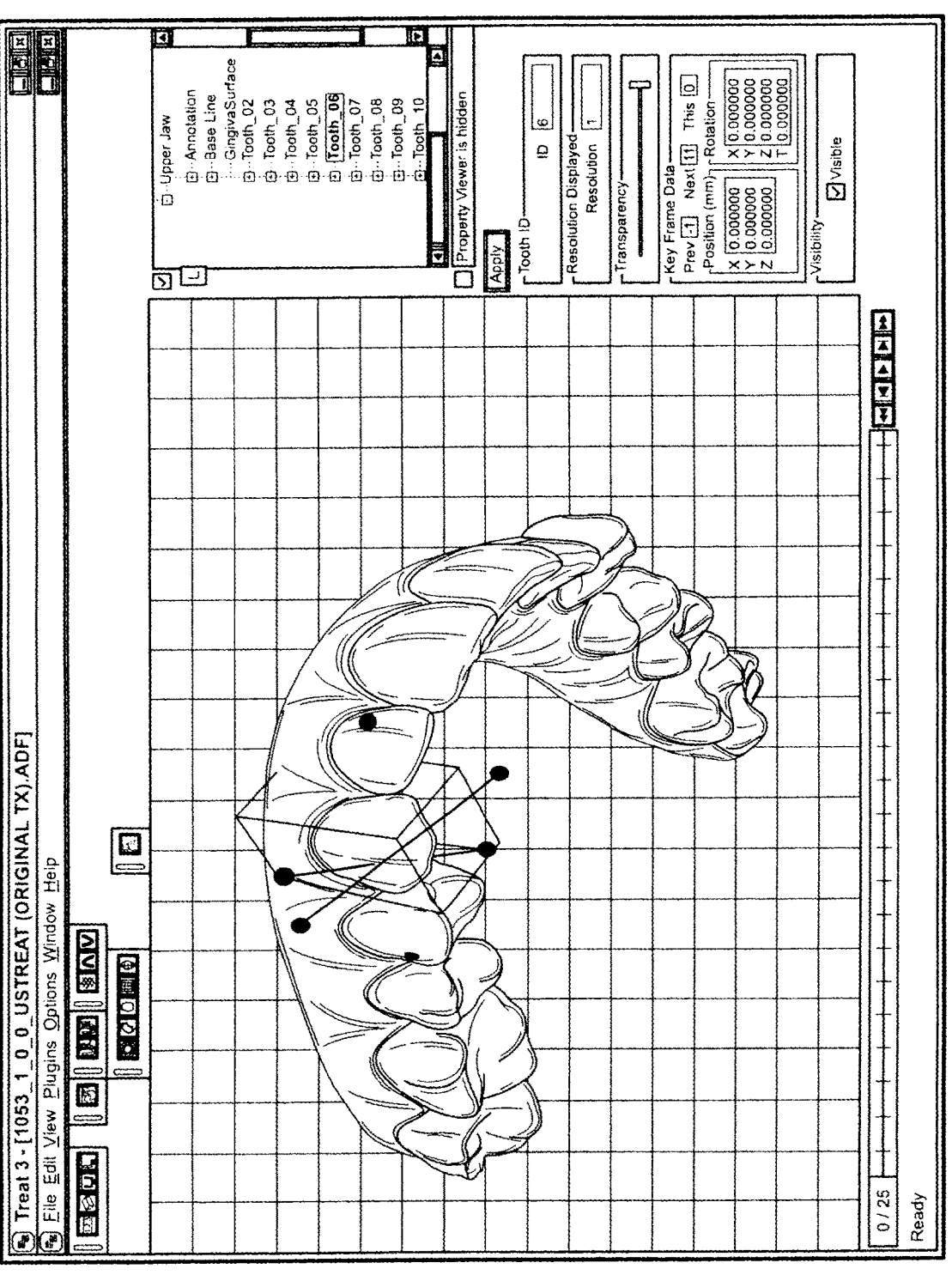
FIG. 10 shows an exemplary user interface showing teeth.

FIG. 10 shows an exemplary user interface showing the erupted teeth, which can be shown with root information in another embodiment. Each tooth is individually adjustable using a suitable handle. In the embodiment of FIG. 10, the handle allows an operator to move the tooth in three-dimensions with six degrees of freedom.

The teeth movement is guided in part using a root-based sequencing system. In one embodiment, the movement is constrained by a surface area constraint, while in another embodiment, the movement is constrained by a volume constraint.

In one embodiment, the system determines a surface area for each tooth model. The system then sums all surface areas for all tooth models to be moved. Next, the system sums all surface areas of all tooth models on the arch. For each stage of teeth movement, the system checks that a predetermined area ratio or constraint is met while the tooth models are moved. In one implementation, the constraint can be to ensure that the surface areas of moving teeth are less than the total surface areas of teeth on an arch supporting the teeth being moved. If the ratio is greater than a particular number such as 50%, the system indicates an error signal to an operator to indicate that the teeth should be moved on a slower basis.

In another embodiment, the system determines the volume for each tooth model. The system then sums the volumes for all tooth models being moved. Next, the system determines the total volume of all tooth models on the arch. For each stage of teeth movement, the system checks that a predetermined volume ratio or constraint is met while the tooth models are moved. In one implementation, the constraint can be to ensure that the volume for moving teeth is less than the volume of all teeth on an arch supporting the teeth being moved. If the ratio is greater than a particular number such as 50%, the system indicates an error signal to an operator to indicate that the teeth should be moved on a slower basis.

Optionally, other features are added to the tooth model data sets to produce desired features in the aligners. For example, it may be desirable to add digital wax patches to define cavities or recesses to maintain a space between the aligner and particular regions of the teeth or jaw. It may also be desirable to add digital wax patches to define corrugated or other structural forms to create regions having particular stiffness or other structural properties. In manufacturing processes that rely on generation of positive models to produce the repositioning appliance, adding a wax patch to the digital model will generate a positive mold that has the same added wax patch geometry. This can be done globally in defining the base shape of the aligners or in the calculation of particular aligner shapes. One feature that can be added is a rim around the gumline, which can be produced by adding a digital model wire at the gumline of the digital model teeth from which the aligner is manufactured. When an aligner is manufactured by pressure fitting polymeric material over a positive physical model of the digital teeth, the wire along the gumlines causes the aligner to have a rim around it providing additional stiffness along the gumline.

In another optional manufacturing technique, two or more sheets of material are pressure fit over the positive tooth model, where one of the sheets is cut along the apex arch of the aligner and the other(s) is overlaid on top. This provides at least a double thickness of aligner material along the vertical walls of the teeth.

The changes that can be made to the design of an aligner are constrained by the manufacturing technique that will be used to produce it. For example, if the aligner will be made by pressure fitting a polymeric sheet over a positive model, the thickness of the aligner is determined by the thickness of the sheet. As a consequence, the system will generally adjust the performance of the aligner by changing the orientation of the model teeth, the sizes of parts of the model teeth, the position and selection of attachments, and the addition or removal of material (e.g., adding virtual wires or creating dimples) to change the structure of the aligner. The system can optionally adjust the aligner by specifying that one or more of the aligners are to be made of a sheet of a thickness other than the standard one, to provide more or less force to the teeth. On the other hand, if the aligner will be made by a rapid prototyping process (e.g., stereo or photo lithography process), the thickness of the aligner can be varied locally, and structural features such as rims, dimples, and corrugations can be added without modifying the digital model of the teeth.

The system can also be used to model the effects of more traditional appliances such as retainers and braces and therefore be used to generate optimal designs and treatment programs for particular patients.

Figures 11A, 11B:
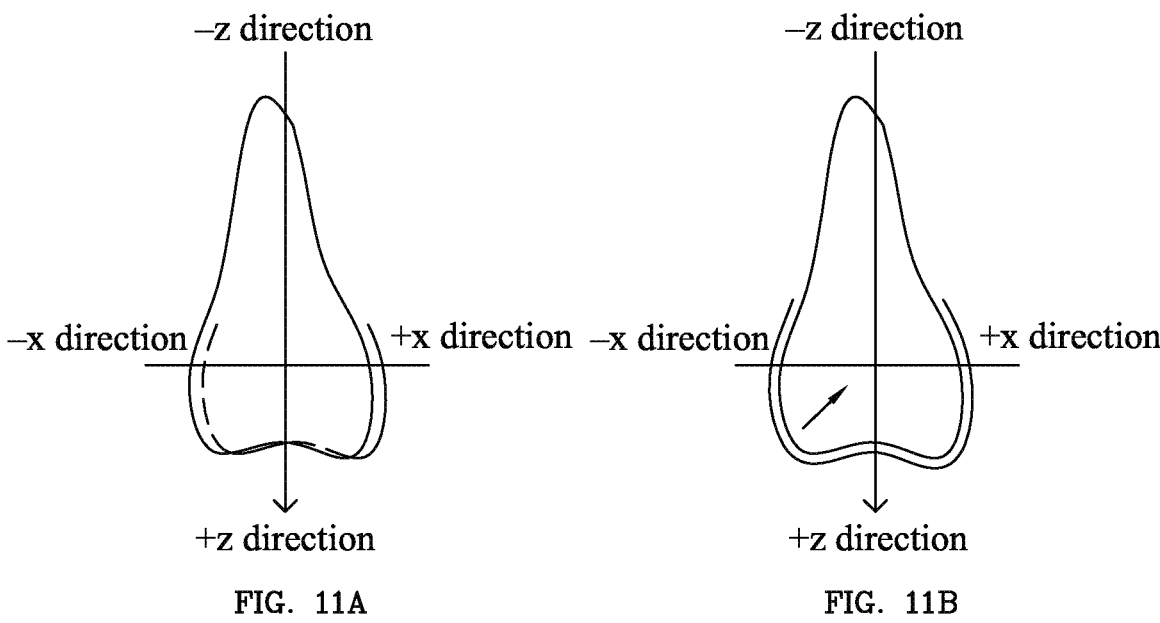
FIGS. 11A and 11B illustrate an initial tooth position with a positioned dental appliance, and a resulting undesirable force vector, respectively.

FIGS. 11A-11B illustrate an initial tooth position with a positioned dental appliance, and a resulting undesirable force vector, respectively. Referring to the Figures, in an example where the tooth as shown is being moved in a facial direction along the x-direction, upon positioning of the dental appliance such as the polymeric shell aligner, over the tooth, the aligner shape geometry is configured to apply a predetermined force upon the tooth to reposition the tooth in accordance with a treatment plan for the particular treatment stage. For example, as shown in FIG. 11B, the dental appliance is configured to engage the tooth to reposition the tooth in the x-direction as shown, but, rather, results in the application of a predetermined force in the +x/−z direction as shown and illustrated by the arrow.

Figures 11C, 11D:
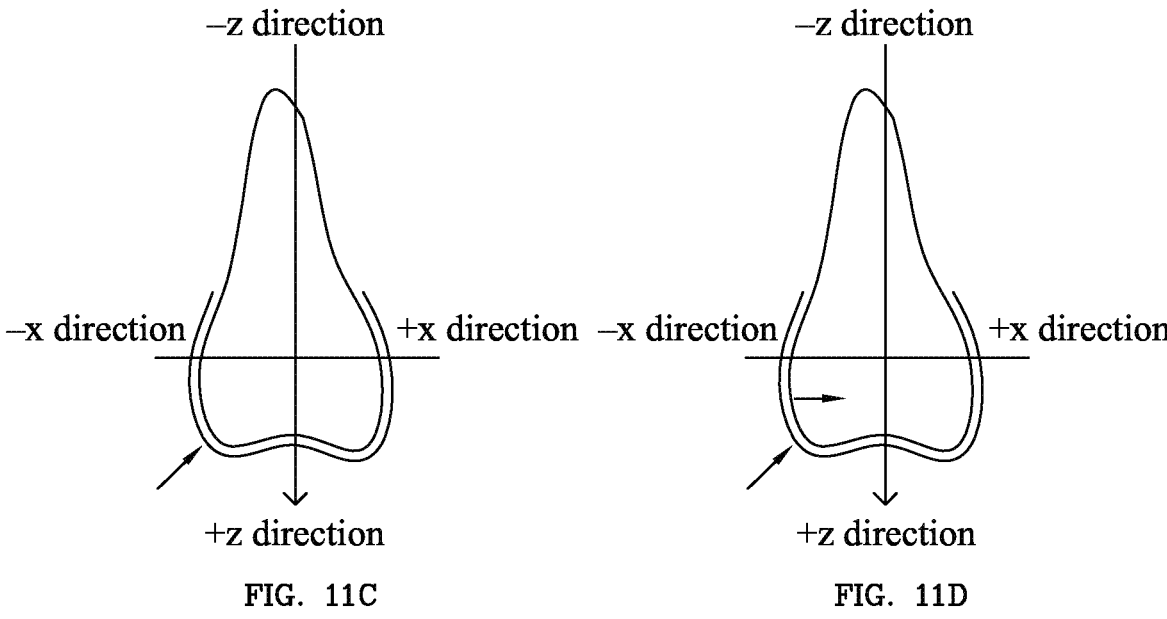
FIGS. 11C and 11D illustrate a relief addition to the dental appliance to counteract the undesirable force vector around the tooth, and the resulting desired application of the predetermined force on the tooth by the dental appliance, respectively.

Accordingly, in one aspect, the aligner shape geometry may be optimized to compensate for the undesirable but resulting force vector so as to counteract its force and further, to apply the intended force in the direction based on the treatment plan for the treatment stage under consideration. That is, FIGS. 11C-11D illustrate a relief addition to the dental appliance to counteract the undesirable force vector around the tooth, and the resulting desired application of the predetermined force on the tooth by the dental appliance, respectively. In one aspect, to compensate for the undesirable force (for example, as shown in FIG. 11B by the arrow), a predetermined relief (for example, but not limited to, 0.1 to 0.3 mm) may be provided such that the contact between the aligner and the tooth that resulted in the undesirable force vector is avoided, but still retaining the desired force, for example, along the x-axis as discussed above.

Referring to FIGS. 11C, the predetermined relief on the aligner is illustrated by the shown arrow, whereby the engagement between the aligner and the tooth at the location resulting in the undesirable force is removed by modifying the shape of the aligner geometry. In this manner, in one aspect, and as shown in FIG. 11D, the intended and desirable force applied upon the tooth for example, in the x-direction, is achieved by, for example, modifying the aligner shape geometry.

Figure 12:
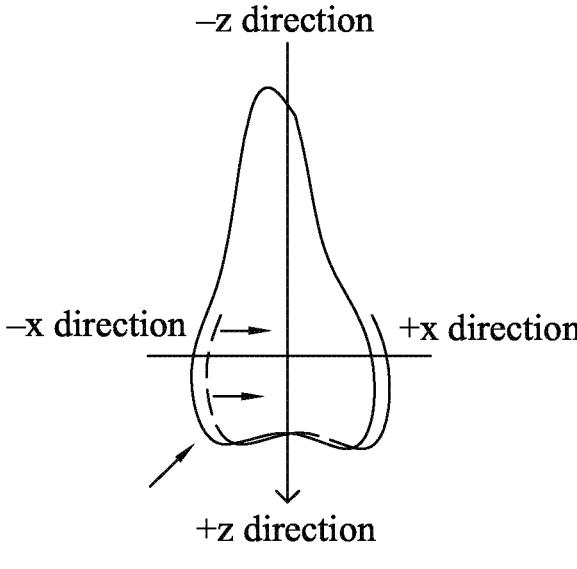
FIG. 12 illustrates a modified dental appliance geometry including an additional shape modification to remove a gap between the dental appliance and the tooth.

FIG. 12 illustrates a modified dental appliance geometry including an additional shape modification to remove a gap between the dental appliance and the tooth. Referring to FIG. 12, it is to be noted that while the modification of the aligner shape geometry (for example, discussed above in conjunction with FIGS. 11C-11D), results in the desired predetermined force applied upon the tooth as planned for the dental treatment, there may be a gap or pocket that forms between the tooth and the aligner, for example, as shown in FIG. 12, near the gingival area. In one aspect, to account for this gap or pocket generated, the aligner shape geometry may be further modified or optimized, for example, to better adapt in the direction towards the tooth when the aligner is in the active (or stretched) state.

Referring to FIG. 12, the optimization of the aligner shape geometry to address the formed gap or pocket is illustrated by the arrow in one embodiment, in the direction of which, the aligner shape may be modified. Moreover, it should be noted that the optimization of the aligner shape to account for the gap may potentially effect the direction of the applied force on the tooth by the aligner, and thus, may further require additional modification or optimization.

In one aspect, the modification of the dental aligner shape geometry with one or more areas of relief, as well as recontouring for looser or tighter adaptation, respectively, to achieve the desired force vector, while avoiding friction and other undesirable force vectors provides improved and customized aligner shape for the treatment of the dental conditions.

In manufacturing of the dental appliances, in one aspect, the mold formed by rapid prototyping may be adjusted during the build process to take shape of the desired geometry based on, for example, digitally adding and/or subtracting the relief and/or protrusion in predefined or relevant locations of the mold.

Figure 13:
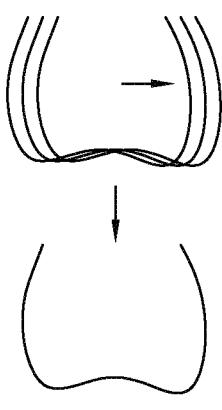
FIG. 13 illustrates dental appliance shape geometry configuration based on sweep geometry of the treatment plan for a tooth.

FIG. 13 illustrates dental appliance shape geometry configuration based on sweep geometry of the treatment plan for a tooth. Referring to FIG. 13, in one aspect, since friction between the dental aligner and the tooth may impose limitations to the treatment, in one aspect, the aligner shape geometry may be optimized by removing all interferences between the current position (at the current treatment stage), and the next position (the n+1 treatment stage). That is, a sweep geometry between the current position and the next position may be generated. The sweep geometry as illustrated in FIG. 13 is the union geometry between the current position and the next infinitely small increment towards the next position (n+1 treatment stage). By adding up the infinitely small increments, the resulting geometry establishes the sweep geometry shape.

Referring again to FIG. 13, after determining the sweep geometry for the aligner to minimize or remove friction between the tooth and the dental aligner, one or more distortions or relief may be added to the aligner shape to provide the desired movement vector to apply the intended force in the direction as determined for the particular treatment stage for the treatment plan.

In a further aspect, it is possible to detect when a tooth movement will be less likely as a result of inadequate force generation. That is, the amount of surface area perpendicular to the desired line of movement (or to the direction of the movement vector) may be insufficient for the aligner to deliver the necessary force. For example, in the extrusive direction (along the +Z axis, as shown in FIG. 12), there may be insufficient undercut present to enable a tooth to be pushed along this direction. As a result, a dental attachment may be added or provided on the tooth to improve the amount of surface area perpendicular to the desired direction of tooth movement.

In one aspect, based on the force behavior determined from the material properties and the amount of surface area perpendicular to the composite vector resulting from the movement vector for the particular treatment stage, additional surface area may be added to the tooth by employing a dental attachment specifically suited for the desired movement. In this manner, in one aspect, the cross section of the surface area may be determined for a particular tooth, and the dental attachment may be positioned thereon, to enhance or improve upon the necessary surface area to cooperate or engage with the dental appliance to effect the desired movement vector or the predetermined level of force upon the tooth in the accurate direction for the treatment stage.

In this manner, in one aspect, a dental aligner may be manufactured or simulated using a computer aided design tool or system, where a representation of the tooth to be moved is first modeled. Thereafter, the aligner that defines the target position of the tooth is modeled with shape geometry properties defined. Thereafter, the force necessary to reposition the tooth from the initial location to the target location is determined or modeled, for example, using FEA modeling or other suitable computation and/or modeling techniques. In one aspect, it is possible to define the force using a physical model of the teeth connected to force measurement sensors, such that the optimal forces may be determined using the readouts obtained from the physical model, and thus altering the shapes of attachments and aligner configurations based at least in part on the feedback from the physical force gauge.

As a result, a movement vector is defined which establishes the direction of the applied force, as well as the level of force and its properties which are necessary to reposition the tooth from the initial position to the target position. Based on the movement vector, and the modeled aligner shape, the aligner is further modified or reconfigured to factor in the determined movement vector. That is, after having defined the movement vector which identifies the force properties necessary for the tooth repositioning, the dental appliance shape is altered or optimized based on the determined movement vector. Additionally, the appliance shape may be further optimized to counteract the undesirable forces or force components that may result based on the defined movement vector.

Thereafter, the modified or optimized dental appliance may be manufactured through rapid prototyping or other suitable techniques to attain the desired tooth movement. Further, this process may be repeated for the optimization of dental appliance for each treatment stage of the treatment plan such that the aligner performance and therefore, the treatment plan result is improved.

Additionally, in one aspect, there is provided an interactive analysis process where minute or small localized changes are introduced into the aligner shape geometry, and wherein the effect of the resulting force profile is compared to the desired force, for example, in each treatment stage of a treatment plan, and repeated if the result is closer to the target profile and ignored if the results move away or deviate further from the target profile. This may be repeated for each treatment stage of the treatment plan such that the series of dental appliances or aligners are each optimized in its respective shape geometry to improve treatment results.

In a further aspect, in one embodiment, the dental appliance configuration may be based on sweep geometry discussed above to minimize friction between the dental appliance and the respective tooth, and further, the dental appliance may be modified to create one or more individual contact points or surfaces (for example, dimples or contacts using attachments bonded to teeth) to generate the desired force. The resulting dental appliance geometry including the current and the subsequent (n+1 stage) sweep path geometry as well as the force generating movements such as the movement vector discussed above, may be modeled using for example, a computer aided design or modeling tool.

Furthermore, in yet still another aspect, dental attachment placement may be determined based on the location of the maximum amount of surface area available perpendicular to the desired direction of the tooth movement. Further, if the force on any given tooth in the treatment plan is at or below a predefined level, the attachment may be added to the tooth to supplement the desired surface area or increase the friction coefficient of the tooth thereby improving the force profile of the aligner of the tooth.

In one aspect, the data set associated with the teeth, gingiva and/or other oral tissue or structures may be intentionally altered through, for example, addition, partial or total subtraction, uniform or non-uniform scaling, Boolean or non-Boolean algorithm, or geometric operations, or one or more combinations thereof, for the configuration, modeling and/or manufacturing of the dental appliance that may be optimized for the desired or intended treatment goal.

Moreover, referring to the discussion above regarding attachments, angulation or the attachment as well as the surface configuration of the attachments may be provided to improve upon the movement vector to optimize its application to the desired tooth while minimizing the amount of undesirable or unwanted force vectors that may be counteracting upon the movement vector. Additionally, in one aspect, a series of abutting attachments may be provided to alter the force direction or generate the movement vector which is carried over for a predetermined time period, such that, the series of abutting attachments may be configured to function as a slow motion cams where the dental appliance then functions as a follower.

In still another aspect, point tracing may be added to treat and/or track tooth points over the treatment stages, such that the desired or proper cam/follower relationship may be determined to attain the target position or the treatment goal. In one aspect, one or more protrusions on the interior surface(s) of the dental appliance may be configured as the follower, and which may be formed from virtual pressure points. The virtual pressure points are comprised in one embodiment of voids intentionally build or designed into the reference mold or model, which is associated with corresponding portions in the aligner that are indented to exert additional pressure on the teeth when the aligner is formed over the reference mold.

Figure 14A:
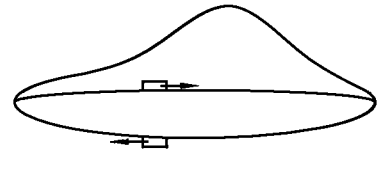
FIGS. 14A and 14B illustrate dental attachment positioning for tooth rotation.
Figure 14B:
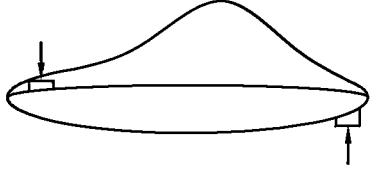

FIGS. 14A-14B illustrate dental attachment positioning for tooth rotation. Referring to FIGS. 14A-14B, a pair of attachments are positioned on buccal and lingual surfaces of a tooth as shown, with the centers positioned in a plane that is perpendicular to the Z-axis relative to the tooth. Referring to the Figures, the two attachments are displaced or biased in opposite directions as shown by the respective arrows in the figures, in the aforementioned plane, to generate a couple, which corresponds to a torque with a zero net force, resulting in a rotational movement of the tooth.

Figure 15:
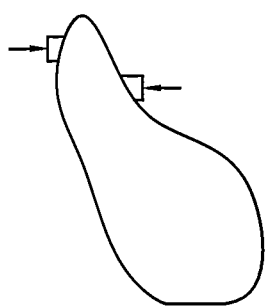
FIG. 15 illustrates dental attachment positioning for tooth inclination.

FIG. 15 illustrates dental attachment positioning for tooth inclination. Referring to FIG. 15, one attachment may be positioned on buccal surface while another attachment is positioned on the lingual surface with a difference in their relative height with the center or axis positioned in a plane perpendicular to the Y-axis of relative to the tooth. Force is applied on the attachments in the direction as shown by the arrows, resulting in a torque along the Y-axis relative to the tooth position, and with the resulting net force being zero. In another aspect, the attachments may be positioned in a plane perpendicular to the Y-axis relative to the tooth. In this manner, the application of force on the attachments to translate one attachment towards the occlusal and the other in the opposite direction in the same plane results in an inclination of the tooth. This approach may be used, for example, in orthodontic root torquing (lingual root inclination), where the center of rotation for the tooth is in the crown and thus the root will be tipped or inclined.

Figure 16:
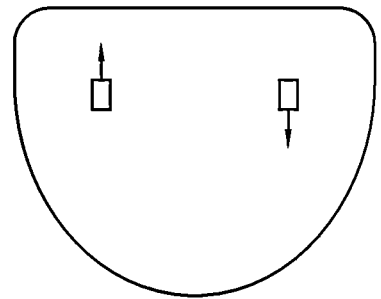
FIG. 16 illustrates dental attachment positioning for tooth angulation.

FIG. 16 illustrates dental attachment positioning for tooth angulation. As shown, the pair of attachments are positioned on the tooth with respective forces applied thereon as shown by the respective arrows. This effect results in the angulation of the tooth (for example, in the clockwise direction in the embodiment shown in FIG. 16).

Figure 17A:
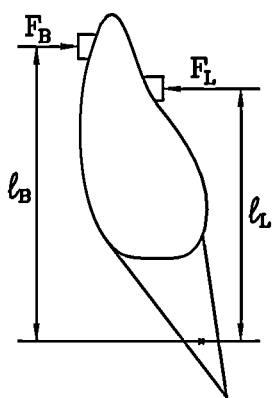
FIGS. 17A and 17B illustrate dental attachment positioning for buccal translation and lingual translation, respectively.
Figure 17B:
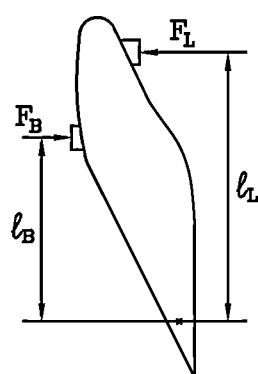

FIGS. 17A-17B illustrate dental attachment positioning for buccal translation and lingual translation, respectively. Referring to the Figures, the pair of attachments as shown may be positioned on both the buccal and lingual sides in an X-Y plane relative to the tooth. With two attachments positioned at different heights to the center of rotation of the tooth, the attachment that is positioned closer to the center of rotation is pushed into the tooth crown more than the attachment that is relatively further away from the center of rotation. Therefore, the total force on the tooth will be a positive value, but the tipping torque may be adjusted to zero, since the force lever component to the center of rotation from each of the two attachments may be adjusted equally opposite to each other. This approach allows for the tooth root translation.

Figure 18A:
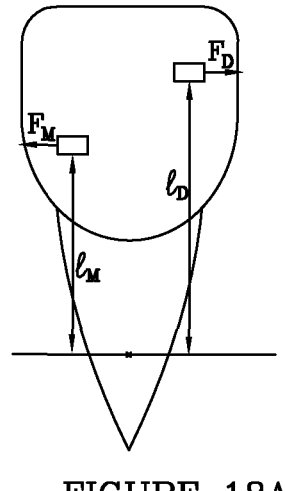
FIGS. 18A and 18B illustrate dental attachment positioning for mesial and distal translation, respectively.
Figure 18B:
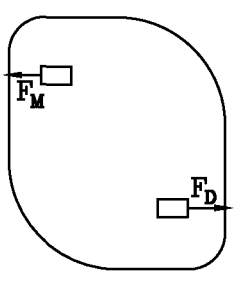

FIGS. 18A-18B illustrate dental attachment positioning for mesial and distal translation, respectively. Referring to the Figures, mesial and distal translation of the tooth may be obtained, for example, by the positioning of the pair of attachments as shown in the Figures, with the suitable predetermined force applied thereon.

Figure 19A:
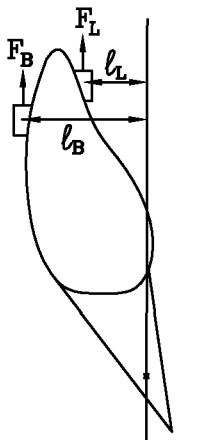
FIGS. 19A and 19B illustrate dental attachment positioning for extrusion and intrusion, respectively.
Figure 19B:
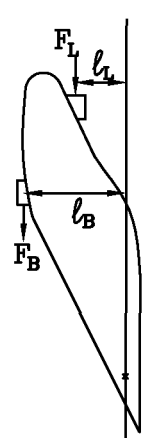

FIGS. 19A-19B illustrate dental attachment positioning for extrusion and intrusion, respectively. Referring to the Figures, the pair of attachments in this case are positioned on the lingual and buccal sides of the tooth, with the centers in the plane that also includes the Z axis. Both attachments as shown are configured to move up along the Z-axis for extrusion or move down along the Z-axis for intrusion. The force generated or applied upon the two attachments are different in magnitude (for example, resulting from different local attachment movement with respect to the tooth crown). When the force from the attachments result in force-lever to the center of rotation that are equally opposite, the tipping torque may be cancelled out, and the resulting force may include extrusion or intrusion translation of the tooth.

Furthermore, the attachment movement resulting in the extrusion or intrusion translation described above may be used with the translation movement on tooth crown to obtain counter-balance torque. For example, the tipping torque resulting from the buccal movement may be counter balanced by configuring an attachment to move relative to the crown to the occlusal plane on the buccal surface.

Additionally, the attachment movement resulting in the extrusion or intrusion translation may be used with locally inflated aligners that include aligner surfaces which are ballooned on some tooth crowns such that the aligner surface does not contact the tooth crowns in a passive state. When an inflated aligner is used with attachment movement for rotation, the maximum rotation torque and minimum unwanted force may be obtained, because the aligner only interferes with attachments to generate a rotation couple with zero total force, for example.

In still a further embodiment, prefabricated attachments may be used to reduce or eliminate failure due to incorrect attachment shape forming.

Accordingly, in one aspect, the n+1 or subsequent/target tooth position is first determined. Thereafter, the direction of movement to reach the target tooth position from the initial tooth position is determined. After determining the direction of movement, the amount or magnitude and direction of force and torque to reposition the tooth from the initial position to the target position is determined. Thereafter, profile of the attachment such as the geometry that would provide the most suitable grip in the direction of the planned tooth movement is determined, as well as the optimal position of the attachment relative to the tooth surface.

Having determined the relevant profile of the attachments, the attachment displacement to attain the position translation from the initial position to the target position is determined. Upon positioning the attachment on the tooth, the dental appliance at the subsequent treatment stage engages with and contacts the dental appliance via the positioned attachment.

In this manner, the force/torque generated by the dental appliance is accurately directed in the desired direction, and also is configured with sufficient magnitude to move the tooth into the next planned position. For example, in one embodiment, the attachments are bonded to the patient's tooth. The initial position of the attachment is determined as described above. The displaced or repositioned attachments may generate a new position of the cavities conforming to the shape of the attachment on the dental appliance. With the attachments on tooth crown at the initial stage and displaced at the subsequent target treatment stage, the dental appliance of the target treatment stage may interfere with the attachment on the tooth at the initial treatment stage. The interference in turn, is configured to generate the force/torque to create the desired tooth movement.

In one aspect, the direction and the magnitude of the force/torque may be modified or optimized to generate counter-balancing force/torque to eliminate or minimize unwanted tipping torque, to attain root movement, and the like, by adjusting the amount of the attachment displacement relative to the crown surface, for example. The amount of the attachment movement with respect to the tooth crown may also be correlated with the tooth movement to generate a treatment plan based on the movement of the attachment.

Figure 20:
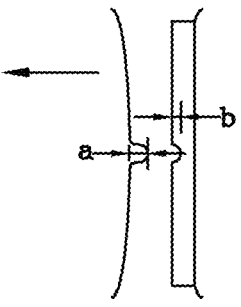
FIG. 20 illustrates a complementary engagement of the dental appliance and the attachment.

FIG. 20 illustrates a complementary engagement of the dental appliance and the attachment. Referring to FIG. 20, in one aspect, a protrusion or a button is provided on the dental appliance such as that shown in FIG. 20 (labeled (a)) which in one embodiment is configured to engage with a corresponding groove or dimple on the attachment (labeled (b)) shown in FIG. 20 and which is positioned on the tooth surface. In this manner, with the button or protrusion on the dental appliance and the cavity on the attachment to receive the protrusion, the relative position of the protrusion may be configured to apply a point or surface area force on the attachment device.

Accordingly, the protrusion on the dental appliance or aligner and the cavity on the receiving attachment device may be configured to form a joint or engagement where point force may be exerted. Furthermore, in the event that the relative position of the protrusion on the dental appliance and the cavity on the attachment is modified locally (for example, based on one or more movement translations discussed above), the point or surface area force may be oriented to cause corresponding tooth movement.

Moreover, in one aspect of the present disclosure, the surface area which is configured to provide the altered tooth facing point force may include a ridge or a flat protrusion inwards towards the tooth. Additionally, the force may also include a "reinforced" surface area at the n+1 stage, where, in one aspect, corrugation may be implemented by one or more ridges or folds, such that the inner surface facing the tooth remains in full contact (rather than to point or ridge) with the tooth and is reinforced in the localized supported area such that the force does not dissipate as easily as in areas where they are unsupported.

Figure 21:
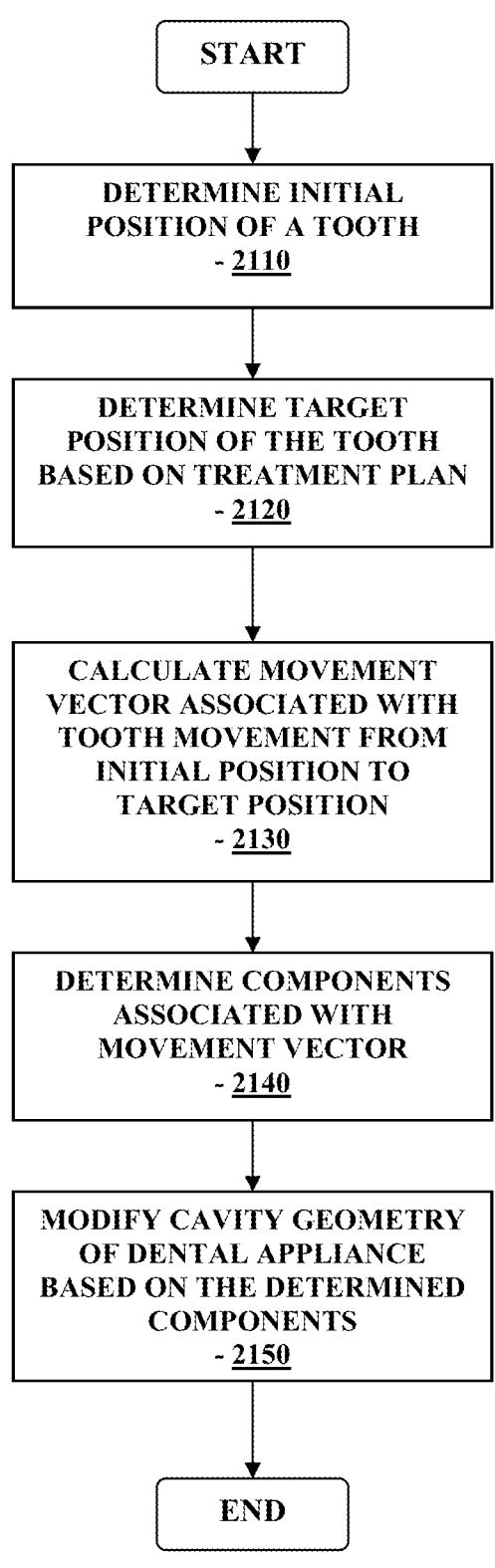
FIG. 21 is a flowchart illustrating the optimized shape geometry of the dental appliance.

FIG. 21 is a flowchart illustrating the optimized shape geometry of the dental appliance. Referring to FIG. 21, at step 2110, the initial position of the tooth is determined. Thereafter, at step 2120, the target position of the tooth based on the treatment plan is determined. In one aspect, the target position may include the next or n+1 treatment stage tooth position. Referring back to FIG. 21, after determining the target position of the tooth based on the treatment plan, a movement vector associated with the tooth movement from the initial position to the target position is calculated or determined at step 2130. That is, a force profile or attribute is determined which includes, for example, the magnitude of the force and the direction of the force, for example, that is associated with the tooth movement from the initial position to the target position.

Referring again to FIG. 21, after determining the movement vector associated with the tooth movement from the initial position to the target position, at step 2140, the components associated with the movement vector are determined. For example, as discussed above, the force magnitude associated with the movement vector to reposition the tooth from the initial position to the target position is determined. Additionally, the force direction for the tooth movement, as well as counter forces for addressing unwanted or unintended forces are determined. Thereafter, based on the determined components associated with the movement vector which is associated with the tooth movement from the initial position to the target position, the cavity geometry of the dental appliance such as the aligner is modified.

Figure 22:
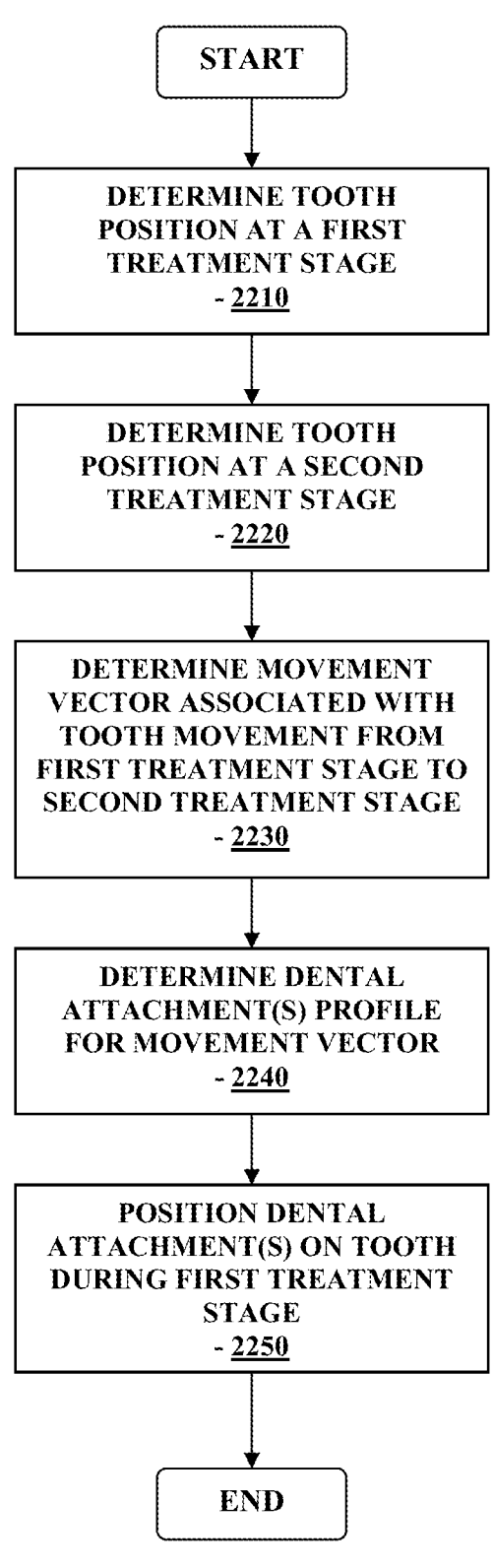
FIG. 22 is a flowchart illustrating the dental attachment positioning.

FIG. 22 is a flowchart illustrating the dental attachment positioning. Referring to FIG. 22, at step 2210 the tooth position at a first treatment stage is determined. At step 2220 the tooth position at the second or n+1 treatment stage is determined. Thereafter, the movement vector associated with the tooth movement from the first treatment stage to the second treatment stage is determined at step 2230. After determining the movement vector associated with the tooth movement, one or more dental attachment profiles associated with the movement vector is determined at step 2240. That is, the position of the dental attachment, the angulation of the dental attachment, the surface area perpendicular to the direction of the force from the dental appliance, for example, are determined. Thereafter, at step 2250, the one or more dental attachments are positioned on the corresponding tooth during the first treatment stage.

In this manner, in one embodiment, the force/torque from the dental appliance is accurately applied to the tooth to reposition the tooth from the initial position to the target or second treatment stage position.

Figure 23:
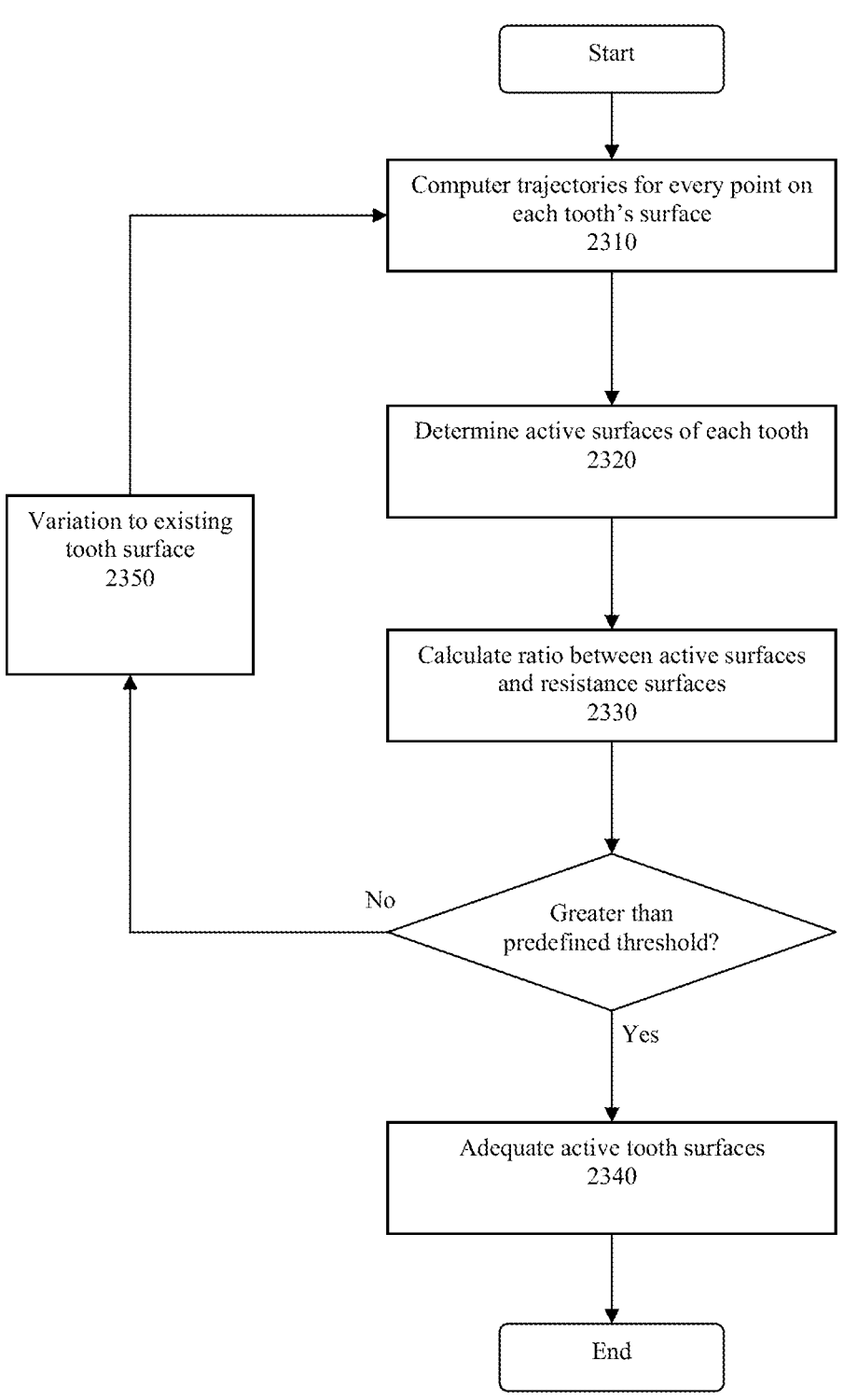
FIG. 23 is a flowchart illustrating a method of moving teeth a predetermined distance and direction based on computing active tooth surfaces.

Referring to FIG. 23, at step 2310, for a stage in the sequence of steps to move teeth from an initial position to a targeted final position, trajectories of every point on each tooth's surface are computed for a given predetermined stage movement. From the trajectories, active surfaces of the teeth are determined 2320. The active surfaces are calculated to be all the points p on tooth surfaces such that the projection of the normal force N(p) to the surface of the tooth at point p onto the tangent vector of the trajectory $\Gamma_p$ corresponding to the desired movement, is greater than a predefined positive threshold. Once the active surfaces are determined, a ratio between the active surfaces and the resistance surface of the roots of the teeth is calculated 2330 for each tooth of the patient. If this ratio is greater than a predefined threshold, then the tooth has adequate active tooth surfaces for the required tooth movement 2340.

Still referring to FIG. 23, if the ratio between the active surfaces and the resistance surfaces of the roots of the teeth is not greater than a predefined threshold, then minimal variation of the existing tooth surface may be done 2350. Variations to the existing tooth surface may include, among others, a custom attachment or appliance to increase the number of active surfaces of the tooth or addition of a material to the surface of the tooth. The minimal variations of the existing tooth surface should satisfy the following constraints; the modified surface provides active surfaces for the required movement with the ratio greater than the threshold between the active surfaces and resistance surfaces, the modified surface is a variation of an accessible surface of the tooth in its current position, and the modified surface must satisfy requirements of manufacturability. Once the existing tooth surface is modified, the new surface is verified with the corresponding aligner to assure that enough contact area with the modified tooth surface exists by repeating steps 2310-2330 for the modified tooth surface.

FIG. 24 is a flowchart illustrating a method of determining whether an attachment is desirable to obtain sufficient active surface area of a tooth. Referring to FIG. 24, at step 2410, for a given treatment stage in the sequence of stages for a treatment plan to move teeth from an initial position to a target position, a rigid body transform A for a tooth may be determined. In one aspect, the rigid body transform A may include a rigid body transformation moving tooth from a position at stage n to a position at stage n+1.

Referring to FIG. 24, from the rigid body transform A, a geodesic curve A(t) in the space of rigid body transforms correlating the rigid body transformation corresponding to zero movement I and the rigid body transform A is determined (2420). For example, in one aspect, the rigid body transform corresponding to zero movement I correlates to where all points remain the same without movement or displacement. For each vertex V on the surface of the tooth, a dot product s (V) of the unit tangent vector to the curve A(t) V at t=0 with inner normal unit vector N to the tooth's surface at V is computed 2430.

Thereafter, the active surfaces of the tooth as the set of all faces of the crown having at least one vertex V where s (V) is greater than a predefined threshold SC is determined (2440). That is, in one aspect, when the angle between the direction of the crown point movement and the surface inner normal at this point is larger than the predefined threshold SC, the crown point may be considered to be active crown surface. Referring again to FIG. 24, the resistance surface of the tooth as the set of all faces of the root having at least one vertex V, where s (V) is smaller than a predefined threshold SR is determined (2450). In a further aspect, if the angle between the direction of root point movement and surface inner normal at this point is larger than the predefined threshold SR, then the root point may be considered to be on the resistance root surface.

Referring still again to FIG. 24, the ratio G may be determined as the ratio of the areas of the active surfaces and resistances surfaces (2460). If the ratio G is greater than the predefined active-to-resistance threshold AR, then no attachment may be needed (2470). For example, in one aspect, if the ratio of area of the crown active surface to the area of root resistance surface is greater than the predefined active-to-resistance threshold AR, the movement may be considered feasible. On the other hand, if the ratio G is not greater than AR, then a minimal addition to the crown surface, such that recomputed ratio G satisfies the condition of G>AR is used (2480). This addition may be made as an attachment, such as a ridge, protrusion, or dimple, among others, and may be engaged to the crown of the tooth.

According to an embodiment, a non-iterative process is used for determining a near-optimal shape of the aligner for the desired movement according to a treatment plan. FIG. 25 is a flowchart of this non-iterative process 800. For an elementary shape feature (e.g., a dimple), the magnitude of the force developed by the feature is computed as a function of the position of the feature on the surface of the aligner and of the feature prominence at step 810. This function may be derived statistically by relating the geometric characteristic of a feature location (e.g., distance to the boundary, distance to the inflection ridge, curvature, etc.) with the value of the magnitude of force generated by the feature. For a given movement of a tooth from stage n to stage n+1, the rotation axis through the center of resistance and translation vector corresponding to the given movement is computed at step 820. Next, at step 830, points on the tooth surface are identified where the forces would be applied, and the magnitude of forces are computed such that, if the forces with these magnitudes are applied at the identified points in the direction of their trajectories of movement from stage n to stage n+1, then the following conditions are met:

a. total torque axis through the center of resistance would be close to the required rotation axis direction b. total torque magnitude would be sufficient for the tooth rotation c. total force direction would be close to direction of translation vector d. total force magnitude would be sufficient for translation of the tooth.

Among the sets of points satisfying the above conditions, the sets of points satisfying the following constraints is then identified at step 840:

a. Number of points is the least possible b. Points are as far apart as possible c. Points as close as possible to the active surface of the tooth.

For the point sets identified in step 840, the surface of the attachments required (if any) to convert the point location into active surface for the required tooth movement is computed at step 850. Then, the point set with no more than one attachment, which is on buccal side of the tooth, with conditions of the step 830 satisfied as close as possible, is chosen at step 860. Then, at step 870, the shape features (e.g., dimples) are created at the identified point set with prominence corresponding to the desired force magnitudes. At optional step 880, if points are located close to each other, the corresponding dimples can be merged to form ridges. The skilled artisan will appreciate that the resulting dimples and ridges are the aligner shape features required for the desired movement of the tooth.

Figure 26:
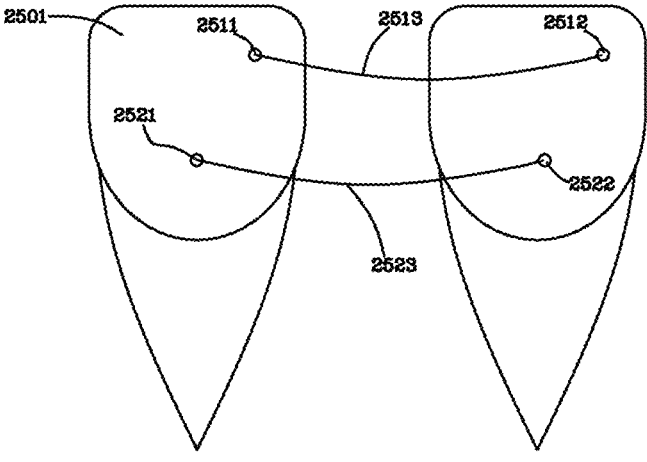
FIG. 26 shows the trajectories of crown points from a first stage to a second stage.

FIG. 26 shows the trajectories of crown points from a first treatment stage to a second treatment stage of a treatment plan in one aspect. Referring to FIG. 26, the crown of a tooth 2501 has points 2511 and 2521 in an initial position of a treatment stage of the treatment plan. At a desired treatment stage of the treatment plan, the equivalent points of the crown of a tooth 2501 may be displaced to target locations 2512 and 2522. The trajectories 2513 and 2523 may be determined and mapped based on the initial and target position of the crown of the tooth.

Figure 27:
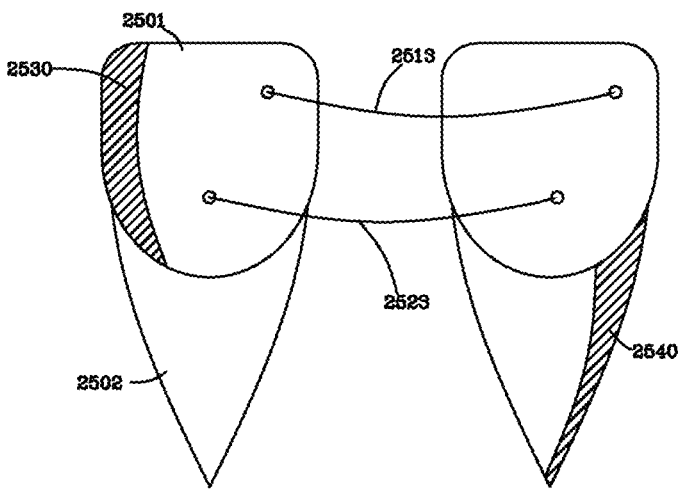
FIG. 27 shows the active surface and resistance surface of a tooth.

FIG. 27 shows the active surface and resistance surface of a tooth in one aspect. Referring to FIG. 27, the crown of a tooth 2501, has active surfaces 2530, or surfaces onto which force may be applied to move a tooth in a desired trajectory 2513 and 2523. Working against these active surfaces may include forces applied on resistance surfaces 2540 located on the root of a tooth 2502. When the ratio of the active surfaces to the resistance surfaces is greater than a predefined threshold, the correct forces may be applied, for example by shaped aligners, to move the tooth along the desired trajectory 2513 and 2523.

Figure 28:
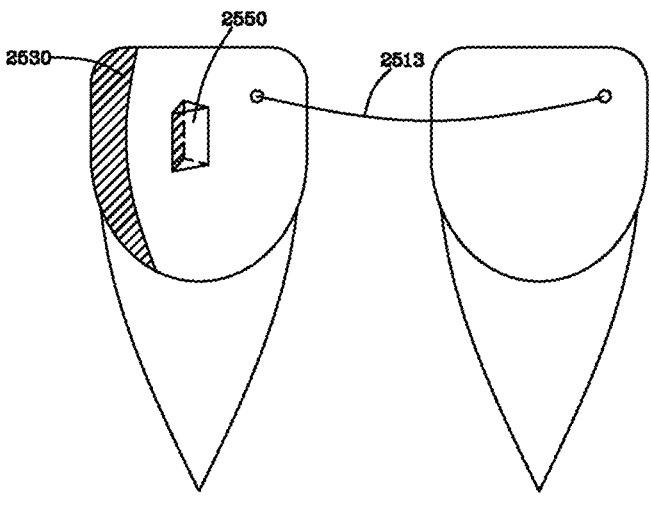
FIG. 28 demonstrates the increase in active surface of a tooth by the addition of an attachment.

FIG. 28 demonstrates the increase in active surface of a tooth by the addition of an attachment. Referring to FIG. 28, in the case where the ratio of active surfaces to resistance surfaces is not initially greater than a predefined threshold, additions, such as attachments 2550 including ridges, dimples, or protrusions, may be engaged to the tooth in order to increase the active surfaces 2530 of a tooth. By increasing the amount of active surfaces 2530 by the use of an attachment, the ratio between the active and resistance surfaces may then be greater than the predefined threshold, thus allowing forces to be applied for the correct movement of a tooth along a desired trajectory 2513.

Figure 29:
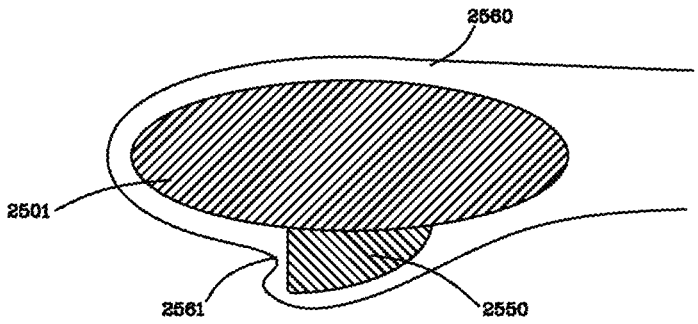
FIG. 29 shows a cross-section of a tooth with an attachment and aligner with a ridge to match the attachment.

FIG. 29 shows a cross-section of a tooth with an attachment and aligner with a ridge to match the attachment. Referring to FIG. 29, in order to achieve a desired tooth movement, sometimes an attachment 2550 may be used to increase the active surface area of a tooth crown's surface 2501. In order for the attachment to be effective, correct forces must be applied to the attachment 2550 in order to move the tooth along the desired trajectory path. These forces are created by ridges 2561, or any equivalent, in a shaped aligner 2560 that fit to the attachment 2550. In this way the aligner 2560 applies the correct forces directly to the tooth surface, as well as to the attachment 2550 in order to move the tooth along the desired trajectory from an initial position to a desired target position.

In the manner described, in one aspect, an orthodontic treatment plan may be generated based at least in part, on the patient's initial dentition in its initial position, and the desired treatment outcome including, for example, the location and orientation of the teeth at the end of the treatment. In one aspect, computer software implemented approach may be used to analyze the path of each tooth from its initial to final position. All movements in three dimensional spaces may be analyzed. For example, the path may be described as a series of incremental movements, where each increment may include a combination of linear displacements and rotations. The loadings-forces and moments-required to accomplish the desired movement may be determined based, for example, at least in part on the loadings that may induce movement through the next increment of movement on the path to the final target position, or may induce one movement which encompasses the total movement from the initial location to the final target position.

In one aspect, the surface of the tooth may be analyzed and defined as a compilation of discrete smaller surfaces. The surfaces with orientations desirable to the required direction or the loading may be identified. If no such surface(s) exists or are not optimal for the required load application, or cannot be accessed intraorally, the tooth surface/orientation may be contoured for improvement or altered by adding material. In this manner, in one aspect, the approach described herein may determine one or more possible solutions to provide correction to the force system desired, and determine one or more clinically viable solutions.

In a further aspect, more than one force on more than one surface may be required to impart the correct force system for the prescribed movement. It will be understood that the dental appliance is configured to apply a force system on a tooth and that a force system comprises at least one of a force, a moment of a force, and a moment of a couple. Accordingly, variations may be made to the aligner geometry such that the designated force system may be delivered on the surfaces as identified, for example, by the one or more viable solutions determined. Variations in aligner geometric parameters may result in variations in the points of contact of the aligner and tooth, and control the force system applied to the particular tooth. The variations may be calibrated to control the force system and initiate tooth movement. Also, specific features such as, but not limited to, ridges, may be included to attain control of contact points on the surfaces and provide the necessary loading.

In yet a further aspect, the aligner geometry may be provided with a relief area or bubble to allow unhindered movement of the tooth into that area or location. The force system applied to the tooth by the aligner may move the tooth unchallenged within the open space encompassed by the aligner.

In still another aspect, the aligner features may be designed and fabricated to limit movement of the tooth. For example, the aligner may be designed to be a physical boundary through which the tooth cannot move providing safety against unwanted movements that may be deleterious to the patient's health. Further, the aligner in another aspect may be configured to function as a guiding surface along which the tooth moves. More particularly, the aligner may be configured to impart a force system to the tooth and the tooth may be guided into a specific location and orientation assisted by the guidance of the aligner.

In this manner, incorporation of one or more features into an aligner geometry or configuration may result in a subsequent change of the geometry of the aligner, the alterations resulting in changes in the location of the contact surfaces of the tooth and the aligner. The changes and the effects of these geometric changes may be determined and compensated by identifying new surfaces and loadings to accomplish the desired movement. The aligner geometry may be improved in such iterative design process as each iteration may be configured to consider each feature and its effect on the aligner geometry, on the surfaces of contact and on the force system produced, before defining the final aligner design, and also, the overall treatment plan including the treatment stages.

In the manner described, in one aspect, orthodontic treatment approach may include defining the path of movement of each tooth, the force system required to attain the movement, determination of the surfaces and the forces to be applied to those surfaces to impart the defined force system, and the geometric designs of aligners that satisfies such treatment criteria.

A computer implemented method in one embodiment includes establishing an initial position of a tooth, determining a target position of the tooth in a treatment plan, calculating a movement vector associated with the tooth movement from the initial position to the target position, determining a plurality of components corresponding to the movement vector, and determining a corresponding one or more positions of a respective one or more attachment devices relative to a surface plane of the tooth such that the one or more attachment devices engages with a dental appliance.

The one or more attachment devices may be configured to apply a predetermined force on the dental appliance substantially at the surface plane of the tooth.

In one aspect, the plurality of components may provide one or more of a rotational displacement of the tooth, an angular displacement of the tooth, a linear displacement of the tooth, or one or more combinations thereof The dental appliance may include a polymeric shell.

Further, one or more of the plurality of components may correspond to a respective one or more force or moment of force applied by the dental appliance on the respective attachment device, where the one or more of the plurality of components may correspond to a respective one or more force or moment of force applied by the respective attachment device on the dental appliance.

The one or more attachment devices may include a plurality of dental attachment devices provided on the tooth in an abutting position relative to each other, where the dental appliance may be configured to physically contact each of the plurality of the abutting dental attachment devices sequentially, and separately for a predetermined period of time.

An apparatus for modeling a dental appliance in another embodiment includes a data storage unit, and a processing unit coupled to the data storage unit and configured to determine an initial position of a tooth, determine a target position of the tooth in a treatment plan, calculate a movement vector associated with the tooth movement from the initial position to the target position, determine a plurality of components corresponding to the movement vector, and determine a corresponding one or more positions of a respective one or more attachment devices relative to a surface plane of the tooth such that the one or more attachment devices engages with a dental appliance.

In one aspect, the one or more attachment devices may be configured to apply a predetermined force on the dental appliance substantially at the surface plane of the tooth.

Further, the plurality of components may provide one or more of a rotational displacement of the tooth, an angular displacement of the tooth, a linear displacement of the tooth, or one or more combinations thereof Moreover, the dental appliance may include a polymeric shell.

The one or more of the plurality of components may include a respective one or more force or moment of force applied by the dental appliance on the respective attachment device, where the one or more of the plurality of components may correspond to a respective one or more force or moment of force applied by the respective attachment device on the dental appliance.

In one aspect, the one or more attachment devices may include a plurality of dental attachment devices provided on the tooth in an abutting position relative to each other, where the dental appliance maybe configured to physically contact each of the plurality of the abutting dental attachment devices sequentially, and separately for a predetermined period of time.

A computer implemented method in accordance with another embodiment includes establishing an initial position of a tooth, determining a target position of the tooth in a treatment plan, calculating a movement vector associated with the tooth movement from the initial position to the target position, determining a plurality of components corresponding to the movement vector, and modifying a cavity geometry of a dental appliance for the tooth based on the plurality of components.

The movement vector may be determined based on FEA modeling. The movement vector may also be based on physical force modeling.

Further, one or more of the plurality of components may include one or more force vectors associated with the movement of the tooth from the initial position to the target position, where the one or more force vectors may be designed into the cavity geometry of the dental appliance to apply the corresponding one or more force associated with the respective one or more force vectors on the tooth.

The method may also include updating the cavity geometry of the polymeric shell for the tooth to apply the determined plurality of components corresponding to the movement vector on the tooth to reposition to the tooth from the initial position to the target position.

In addition, the method may also include determining the level of force associated with the movement vector, where determining the level of force may include determining one or more positions on the tooth surface to apply the movement vector and configuring the cavity geometry of the polymeric shell for the tooth to apply the movement vector at the determined one or more positions on the tooth surface.

A method of manufacturing a dental appliance in accordance with still another embodiment includes determining a treatment plan of a patient's orthodontic condition, for each stage of the treatment plan, defining an initial position of a tooth, determining a target position of the tooth, calculating a movement vector associated with the movement of tooth from the initial position to the target position, determining a plurality of components corresponding to the movement vector, and modifying a cavity geometry of a polymeric shell for the tooth based on the plurality of components.

The method in one aspect may include generating a virtual representation of the modified cavity geometry.

A computer implemented method in accordance with still another embodiment may include establishing an initial position of a tooth, determining a target position of the tooth in a treatment plan, determining a sweep geometric path between the initial position and the target position and an associated movement vector for repositioning the tooth from the initial position to the target position, and modifying a cavity geometry of a polymeric shell for the tooth based on the determined sweep geometric path, where modifying the cavity geometry may include defining one or more contact points on an inner surface of the polymeric shell for the tooth to contact a corresponding predetermined one or more surfaces of the tooth.

Moreover, in still another aspect, modifying the cavity geometry may include defining one or more protrusions on an inner surface of the polymeric shell for the tooth, wherein the one or more protrusions is associated with the movement vector.

The one or more protrusions may include a dimple.

Moreover, the cavity geometry may be modified to minimize friction between an inner surface of the polymeric shell and the tooth.

A computer implemented method in accordance with still yet another embodiment may include establishing an initial position of a tooth, determining a target position of the tooth in a treatment plan, calculating a movement vector associated with the tooth movement from the initial position to the target position, determining a plurality of components corresponding to the movement vector, and determining one or more positions for the placement of a corresponding one or more dental attachment devices based on a respective surface area determination of each of the determined plurality of components corresponding to the movement vector.

In one aspect, the inner surface of a polymeric shell associated with the treatment plan may be configured to apply a respective one or more forces corresponding to the respective one of the plurality of components.

The method in one aspect may include determining a surface area substantially perpendicular to the direction of the movement vector associated with the tooth movement from the initial position to the target position.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse.

The computer system can be programmed to provide a graphical user interface through which computer programs interact with users. The computer system can be programmed to provide a virtual reality, three-dimensional display interface.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An orthodontic aligner of a series of orthodontic aligners, the orthodontic aligner produced by a process comprising:
   receiving a first position of at least one tooth of a patient for a first treatment stage of plurality of orthodontic treatment stages;
   determining a movement vector having a magnitude and a direction for moving the at least one tooth from the first position towards a second position;
   determining a first vertical position relative to the at least one tooth of a first attachment, the first attachment being located on a buccal surface of the at least one tooth;
   determining a second vertical position relative to the at least one tooth of a second attachment, the second vertical position different than the first vertical position, the second attachment being located on the buccal surface of the at least one tooth;
   analyzing a surface of the at least one tooth of the patient based on the movement vector;
   designing a first orthodontic aligner of a series of orthodontic aligners having a first attachment receiving cavity at a first location corresponding to the first vertical position of the first attachment and a second attachment receiving cavity at a second location corresponding to the second vertical position of the second attachment and a shape based on the analysis of the surface of the at least one tooth of the patient so that a physical orthodontic aligner having the shape, when in position on teeth of the patient at the first treatment stage, moves the at least one tooth from the first position towards the second position along the movement vector; and
   fabricating the physical orthodontic aligner.

2. The series of orthodontic aligners of claim 1, wherein determining the movement vector for moving the at least one tooth comprises determining trajectories of points of the at least one tooth from the first position towards the second position.

3. The series of orthodontic aligners of claim 2, further comprising determining a force system for moving the at least one tooth based on the movement vector and the second position.

4. The series of orthodontic aligners of claim 3, wherein analyzing the surface of the at least one tooth includes identifying surface locations with orientations relative to the movement vector for moving the tooth.

5. The series of orthodontic aligners of claim 4, wherein analyzing the surface of the at least one tooth comprises identifying surface locations with desirable orientations relative to the one or more forces for imparting the force system.

6. The series of orthodontic aligners of claim 5, wherein identifying surface locations with desirable orientations relative to the one or more forces for imparting the force system includes determining one or more active surfaces of the tooth relative to the force system.

7. The series of orthodontic aligners of claim 6, further comprising determining that the one or more active surfaces are insufficient for the one or more forces for imparting the force system and, in response, contouring a model of the surface of the at least one tooth with an addition of material to improve an amount of surface with desirable orientations for the one or more forces and designing the shape based on the model of the surface of the at least one tooth with the addition of material that improves the amount of surface with desirable orientations for the one or more forces.

8. The series of orthodontic aligners of claim 7, wherein determining that the identified surface locations with desirable orientations is insufficient comprises comparing the active surfaces to a resistance surface of the at least one tooth.

9. The series of orthodontic aligners of claim 8, wherein comparing the identified surface locations with desirable orientations to the resistance surface of the at least one tooth comprises comparing a ratio of the identified surface locations with desirable orientations to the resistance surface of the at least one tooth to a predefined threshold and wherein determining that the identified surface locations with desirable orientations is insufficient for the one or more forces for imparting the force system comprises determining that the ratio of the identified surface locations with desirable orientations to the resistance surface of the at least one tooth is below the predefined threshold.

10. The series of orthodontic aligners of claim 7, wherein contouring the model of surface of the at least one tooth includes contouring the at least one tooth to include a shape of the first attachment.

11. A method of fabricating an orthodontic aligner of a series of orthodontic aligners for moving at least one tooth of a patient according to a treatment plan, the method comprising:

receiving a first position of at least one tooth of a patient for a first treatment stage of a plurality of orthodontic treatment stages;

determining a movement vector having a magnitude for moving the at least one tooth from a first position towards a second position in a mesial or distal direction;

determining a first dental attachment profile of a first attachment, the first dental attachment profile associated with the movement vector and comprising a first dental attachment position and a first dental attachment angulation the first dental attachment position including a first vertical position relative to the at least one tooth of the first attachment, the first attachment being located on a buccal surface of the at least one tooth;

determining a second vertical position relative to the at least one tooth of a second attachment, the second vertical position different than the first vertical position, the second attachment being located on the buccal surface of the at least one tooth;

designing the orthodontic aligner having a shape based on the first dental attachment profile so that a physical orthodontic aligner having the shape, when in position on teeth of the patient at the first treatment stage, moves the at least one tooth from the first position towards the second position along the movement vector; and fabricating the physical orthodontic aligner.

12. The method of claim 11, wherein determining the movement vector for moving the at least one tooth comprises determining trajectories of points of the at least one tooth from the first position towards the second position.

13. The method of claim 12, further comprising determining a force for moving the at least one tooth based on the movement vector and the second position.

14. The method of claim 13, further comprising:

identifying surface locations with desirable orientations relative the force.

15. The method of claim 14, wherein identifying surface locations with desirable orientations relative to the force for imparting the force includes determining one or more active surfaces of the tooth relative to the force.

16. The method of claim 15, further comprising determining that the one or more active surfaces are insufficient for imparting the force and, in response, wherein determining a dental attachment profile includes contouring a model of a surface of the at least one tooth with an addition of material to improve an amount of surface with desirable orientations for the force and designing the shape based on the model of the surface of the at least one tooth with the addition of material that improves the amount of surface with desirable orientations for the force.

17. The method of claim 16, wherein determining that the identified surface locations with desirable orientations is insufficient comprises comparing the active surfaces to a resistance surface of the at least one tooth.

18. The method of claim 17, wherein comparing the identified surface locations with desirable orientations to the resistance surface of the at least one tooth comprises comparing a ratio of the identified surface locations with desirable orientations to the resistance surface of the at least one tooth to a predefined threshold and wherein determining that the identified surface locations with desirable orientations is insufficient for imparting the force comprises determining that the ratio of the identified surface locations with desirable orientations to the resistance surface of the at least one tooth is below the predefined threshold.

19. The method of claim 16, wherein contouring the model of the surface of the at least one tooth includes determining an attachment location on the surface of the at least one tooth.

20. A method of fabricating an orthodontic aligner of a series orthodontic aligners for moving at least one tooth of a patient according to a treatment plan, the method comprising:

determining a first position of at least one tooth of a patient for a first treatment stage of plurality of orthodontic treatment stages and a second position of the at least one tooth;

determining a movement vector for moving the at least one tooth from the first position towards the second position by determining trajectories of points of the at least one tooth from the first position towards the second position;

analyzing a shape of a surface of a crown of the at least one tooth of the patient based on the movement vector to identify active surfaces of the at least one tooth;

determining, based on the active surfaces and the movement vector, that surface shape of a crown of the at least one tooth is insufficient for moving the at least one tooth, wherein determining that the surface shape of the crown of the at least one tooth is insufficient includes comparing the active surfaces to a resistance surface of the at least one tooth, wherein comparing the active surfaces with the resistance surface of the at least one tooth comprises comparing a ratio of the active surfaces with desirable orientations to the resistance surface of the at least one tooth to a predefined threshold and wherein determining that the active surfaces is insufficient for moving the tooth comprises determining that the ratio of the active surfaces to the resistance surface of the at least one tooth is below the predefined threshold;

contouring the at least one tooth, when the surface of the at least one tooth are insufficient for moving the at least one tooth, to adjust the active surfaces of the at least one tooth, wherein contouring includes an addition of material to improve an amount of the active surfaces and designing the shape based on the surface of the at least one tooth with the addition of material that improves the amount of the active surfaces;

designing a first orthodontic aligner of the series of orthodontic aligners to have a shape based on the contouring of the at least one tooth of the patient so that the first orthodontic aligner, when worn by the patient, moves the at least one tooth from the first position towards the second position along the movement vector; and fabricating the series of orthodontic aligners including the first orthodontic aligner.

* * * * *